US006863211B2

(12) United States Patent
Moore et al.

(10) Patent No.: US 6,863,211 B2
(45) Date of Patent: Mar. 8, 2005

(54) OMEGA-HYDROFLUOROALKYL ETHERS, PRECURSOR CARBOXYLIC ACIDS AND DERIVATIVES THEREOF, AND THEIR PREPARATION AND APPLICATION

(75) Inventors: George G. I. Moore, Afton, MN (US); Richard M. Flynn, Mahtomedi, MN (US); Miguel A. Guerra, Woodbury, MN (US); John G. Owens, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 188 days.

(21) Appl. No.: 10/241,901

(22) Filed: Sep. 12, 2002

(65) Prior Publication Data

US 2003/0166487 A1 Sep. 4, 2003

Related U.S. Application Data

(60) Division of application No. 09/789,788, filed on Feb. 20, 2001, now Pat. No. 6,491,983, which is a division of application No. 09/452,711, filed on Dec. 2, 1999, now Pat. No. 6,214,253, which is a division of application No. 09/151,857, filed on Sep. 11, 1998, now Pat. No. 6,024,176, which is a division of application No. 08/881,347, filed on Jun. 24, 1997, now Pat. No. 6,204,299, which is a division of application No. 08/440,450, filed on May 12, 1995, now Pat. No. 5,658,962, which is a continuation-in-part of application No. 08/246,962, filed on May 20, 1994, now Pat. No. 5,476,974.

(51) Int. Cl.$^7$ ................... C07C 19/08; B23K 31/02; B23K 35/34
(52) U.S. Cl. ................... 228/234.2; 510/412; 510/407; 134/40; 134/42
(58) Field of Search .................. 510/407, 412, 510/411; 134/40, 42; 228/234.2, 180.1; 570/130; 252/364

(56) References Cited

U.S. PATENT DOCUMENTS

| 2,713,593 A | 7/1955 | Brice et al. |
|---|---|---|
| 3,214,478 A | 10/1965 | Milian, Jr. |
| 3,250,808 A | 5/1966 | Moore et al. |
| 3,342,875 A | 9/1967 | Selman et al. |
| 3,393,228 A | 7/1968 | Braun |
| 3,493,581 A | 2/1970 | Heinrich et al. |
| 3,598,359 A | 8/1971 | Smith |
| 3,674,800 A | 7/1972 | Sweeney et al. |
| 3,706,773 A | 12/1972 | Anello et al. |
| 3,766,274 A | 10/1973 | Anello et al. |
| 3,787,351 A | 1/1974 | Olson et al. |
| 3,903,012 A | 9/1975 | Brandreth |
| 3,911,138 A | 10/1975 | Clark, Jr. |
| 3,962,439 A | 6/1976 | Yokoyama et al. |
| 3,962,460 A | 6/1976 | Croix et al. |
| 4,094,911 A | 6/1978 | Mitsch et al. |
| 4,110,474 A | 8/1978 | Lagow et al. |
| 4,118,421 A | 10/1978 | Martini |
| 4,169,807 A | 10/1979 | Zuber |
| 4,173,654 A | 11/1979 | Scherer |
| 4,186,253 A | 1/1980 | Yokoyama et al. |
| 4,187,252 A | 2/1980 | Lagow et al. |
| 4,252,827 A | 2/1981 | Yokoyama et al. |
| 4,357,282 A | 11/1982 | Anderson et al. |
| 4,423,077 A | 12/1983 | Slovieter |
| 4,443,480 A | 4/1984 | Clark, Jr. |
| 4,534,978 A | 8/1985 | Yokoyama et al. |
| 4,686,024 A | 8/1987 | Scherer, Jr. et al. |
| 4,729,856 A | 3/1988 | Bornengo et al. |
| 4,847,427 A | 7/1989 | Nappa |
| 4,865,836 A | 9/1989 | Long, Jr. |
| 4,866,096 A | 9/1989 | Schweighardt |
| 4,868,318 A | 9/1989 | Scherer, Jr. et al. |
| 4,871,109 A | * 10/1989 | Kalota et al. ............. 228/180.1 |
| 4,940,814 A | 7/1990 | Schwertfeger |
| 4,973,716 A | 11/1990 | Calini et al. |
| 5,023,362 A | 6/1991 | Krespan |
| 5,053,536 A | 10/1991 | Bierschenk et al. |
| 5,055,138 A | 10/1991 | Slinn |
| 5,077,036 A | 12/1991 | Long, Jr. |
| 5,089,152 A | 2/1992 | Flynn et al. |
| 5,093,432 A | 3/1992 | Bierschenk et al. |
| 5,104,034 A | 4/1992 | Hansen et al. |
| 5,118,494 A | 6/1992 | Schultz et al. |
| 5,125,978 A | 6/1992 | Flynn et al. |
| 5,137,932 A | 8/1992 | Behme et al. |
| 5,185,473 A | 2/1993 | Meyer |
| 5,202,480 A | 4/1993 | Bierschenk et al. |
| 5,210,106 A | 5/1993 | Dams et al. |
| 5,262,082 A | 11/1993 | Janulis et al. |
| 5,476,974 A | 12/1995 | Moore et al. |

FOREIGN PATENT DOCUMENTS

| CA | 0 890 944 | 1/1972 |
|---|---|---|
| DE | 26 50 586 | 5/1977 |

(List continued on next page.)

OTHER PUBLICATIONS

Clark, Jr. et al., "Emulsions of perfluorinated solvents for intravascular gas transport," Federation Proceedings, vol. 34, No. 6, pp. 1468–1477 (1975).

Yokoyama et al., "A Perfluorochemical Emulsion as an Oxygen Carrier," Artificial Organs, vol. 8, No. 1, pp. 34–40 (1984).

(List continued on next page.)

Primary Examiner—Gregory Webb
(74) Attorney, Agent, or Firm—William G. Ewert; Lucy C. Weiss

(57) ABSTRACT

Normally liquid, omega-hydrofluoroalkyl ether compounds (and selected mixtures thereof) have a saturated perfluoro-aliphatic chain of carbon atoms interrupted by one or more ether oxygen atoms. The compounds can be prepared, e.g., by decarboxylation of the corresponding fluoroalkyl ether carboxylic acids and are useful, e.g., in cleaning and drying applications.

7 Claims, No Drawings

FOREIGN PATENT DOCUMENTS

| | | |
|---|---|---|
| EP | 0 231 091 | 8/1985 |
| EP | 0 158 996 | 10/1985 |
| EP | 0 211 237 | 2/1987 |
| EP | 0 261 501 | 3/1988 |
| EP | 0 307 087 | 3/1989 |
| EP | 0 326 539 | 8/1989 |
| EP | 0 450 855 | 10/1991 |
| EP | 0 482 938 | 4/1992 |
| FR | 1 373 014 | 8/1964 |
| FR | 2 620 445 | 3/1989 |
| GB | 1 194 431 | 6/1970 |
| GB | 1 354 138 | 5/1974 |
| GB | 1 549 038 | 7/1979 |
| JP | 48-46583 | 7/1973 |
| JP | 2-169532 | 6/1990 |
| JP | 5-271692 | 10/1993 |
| WO | WO 89/10118 | 11/1989 |
| WO | WO 90/01901 | 3/1990 |
| WO | WO 90/03357 | 4/1990 |
| WO | WO 90/06296 | 6/1990 |
| WO | WO 92/02560 | 2/1992 |
| WO | WO 92/22678 | 12/1992 |
| WO | WO 93/01798 | 2/1993 |
| WO | WO 93/11868 | 6/1993 |
| WO | WO 93/24586 | 12/1993 |

OTHER PUBLICATIONS

Yamanouchi et al., "Quantitative Structure–in Vivo Half–Life Relationships of Perfluorochemicals for Use as Oxygen Transporters," Chem. Pharm. Bull., vol. 33, No. 3, pp. 1221–1231 (1985).

Riess et al., "Design, Synthesis and Evaluation of Fluorocarbons and Surfactants for in Vivo Applications New Perfluoroalkylated Polyhydroxylated Surfactants," Biomat., Art, Cells, Art, Org., vol. 16, Nos. 1–3, pp. 421–430 (1988).

Kawamura et al., "A New Simple Two Layer (Euro–Collins' Solution/Perfluorochemical) Cold Storage Method for Pancreas Preservation," Transplantation Proceedings, vol. 21, No. 1, pp. 1376–1377 (1989).

Segel et al., "Albumin improves stability and longevity of perfluorochemical–perfused hearts," American Physiological Society, 254, pp. H1105–H1112 (1988).

Segel et al., "Prolonged support of working rabbit hearts using Fluosol–43 or erythrocyte media," American Physiological Society, 252, pp. H349–H359 (1987).

Segel et al., "Isolated working rat heart perfusion with perfluorochemical emulsion Fluosol–43," American Physiological Society, 242, pp. H485–H489 (1982).

Teicher et al., "Oxygen–carrying Perfluorochemical Emulsion as an Adjuvant to Radiation Therapy in Mice," Cancer Research, vol. 44, pp. 5285–4288 (1984).

Teicher et al., "Effects of Dose and Scheduling on Growth Delay of the Lewis Lung Carcinoma Produced by the Perfluorochemical Emulsion, Fluosol–DA®," Int. J. Radiation Oncology Biol. Phys., vol. 12, pp. 1311–1313 (1986).

Rockwell et al., Reactions of Tumors and Normal Tissues in Mice to Irradiation in the Presence and Absence of a Perfluorochemical Emulsion, Int. J. Radiation Oncology Biol. Phys., vol. 12, pp. 1315–1318 (1986).

Teicher et al., "Perfluorochemical Emulsions Can Increase Tumor Radiosensitivity," Science, vol. 223, pp. 934–936 (1984).

Teicher et al., "Effect of Various Oxygenation Conditions and Fluosol–DA on Cytotoxicity and Antitumor Activity of Bleomycin in Mice," J. Natl, Cancer Inst., vol. 80, No. 8, pp. 599–603 (1988).

Virmani et al., "Myocardial protection by perfluorochemical infusion during transient ischemia produced by balloon coronary occlusion," Am. Heart J., vol. 226, pp. 421–431 (1988).

Jaffe et al., "Preservation of left ventricular ejection fraction during percutaneous transluminal coronary angioplasty by distal transcatheter coronary perfusion of oxygenated Fluosol DA 20%," Am. Heart J., vol. 115, pp. 1156–1164 (1988).

Cleman et al., "Prevention of ischemia during percutaneous transluminal coronary angioplasty by transcatheter infusion of oxygenated Fluosol DA 20%," Circulation, vol. 74, No. 3, pp. 555–562 (1986).

Anderson et al., "Distal coronary artery perfusion during percutaneous transluminal coronary angioplasty," Am. Heart J., vol. 110, pp. 720–726 (1984).

Peerless et al., "Modification of Cerebral Ischemia With Fluosol," Stroke, vol. 16, pp. 38–43 (1985).

Osterholm et al., "Severe Cerebral Ischemia Treatment by Ventriculosubarachnoid Perfusion with an Oxygenated Fluorocarbon Emulsion," Neurosurgery, vol. 13, No. 4, pp. 381–387 (1983).

Peerless et al., "Protective Effect of Fluosol–DA in Acute Cerebral Ischemia," Stroke, vol. 12, No. 5, pp. 558–563 (1981).

Forman et al., "Reduction of Infarct size with introcoronary perfluorochemical in a canine preparation of reperfusion," Ciculation, vol. 71, No. 5, pp. 1060–1068 (1985).

Zurer, "Looming Ban on Production of CFCs, Halons Spurs Switch to Substitutes," Chemical and Engineering News, pp. 12–18 (1993).

Adcock et al., "Fluorinated Ethers—A New Family of Halons," 1991 CFC Conference Proceedings (1991).

Denson et al., "Synthesis of Some Perfluoroalkylether Compounds," Journal of Fluorine Chemistry, vol. 10, No. 1. Pp. 75–80 (1977).

Croft et al., "Fluoroalkyl–s–triazines," Journal of Heterocyclic Chemistry, vol. 10, No. 6, pp. 943–946 (1973).

Hu et al., "Mechanistic Study on the Photooxidation of Perhalofluoroalkyl Sulfinates," Tetrahedron Letters, vol. 30, No. 48, pp. 6717–6720 (1989).

Berenblit et al., "Synthesis and Some Transformations of Derivatives of Perfluoroalkoxycarboxylic Acids," Journal of Organic Chemistry of the USSR, vol. 15, No. 7, pp. 1264–1271 (1979).

Hegde et al., Synthesis and Herbicidal Activity of 5–(Haloalkyl)–Substituted Thiazolo [4,5–b] pyridine–3(2H)–Acetic Acid Derivatives, vol. 41, No. 11, 1993, pp. 2131–2134, XP002266944.

\* cited by examiner

OMEGA-HYDROFLUOROALKYL ETHERS, PRECURSOR CARBOXYLIC ACIDS AND DERIVATIVES THEREOF, AND THEIR PREPARATION AND APPLICATION

STATEMENT OF PRIORITY

This is a division of application Ser. No. 09/789,788, filed on Feb. 20, 2001, now U.S. Pat. No. 6,491,983 which is a division of application Ser. No. 09/452,711, filed on Dec. 2, 1999, now U.S. Pat. No. 6,214,253, which was a division of application Ser. No. 09/151,857 filed Sep. 11, 1998, now U.S. Pat. No. 6,024,176, which was a division of application Ser. No. 08/881,347 filed Jun. 24, 1997, now U.S. Pat. No. 6,204,299, which was a division of application Ser. No. 08/440,450 filed May 12, 1995, now U.S. Pat. No. 5,658,962, which was a continuation-in-part of application Ser. No. 08/246,962 filed May 20, 1994, now U.S. Pat. No. 5,476,974.

This invention relates to omega-hydrofluoroalkyl ethers and their preparation and application. In another aspect, this invention relates to perfluoro-(alkoxyalkanoic) acids and derivatives thereof and their preparation. In another aspect, it relates to the preparation of perfluoro(alkoxyalkanoic) acids by direct fluorination of their hydrocarbon alkanoic acid or ester analogs and to the preparation of omega-hydrofluoroalkyl ethers, for example, by decarboxylation of said acids or their alkyl esters. In another aspect, this invention relates to uses of perfluoro(alkoxyalkanoic) acids and derivatives thereof.

Because of a steady flow of bad news about the damaged stratospheric ozone layer, the deadlines for the end to industrialized countries' production of chlorofluorocarbons ("CFCs") and other ozone-depleting chemicals were accelerated by countries who are parties to the Montreal Protocol on Substances That Deplete the Ozone Layer—see Zurer, P. S., "Looming Ban on Production of CFCs, Halons Spurs Switch to Substitutes," Nov. 15, 1993, *Chemical & Engineering News*, p. 12.

Work is under way to replace CFCs and halons, such as $CCl_2F_2$, $CCl_3F$, $CF_3Br$, and $CCl_2FCClF_2$, with substitute or alternative compounds and technologies. A number of hydrofluorocarbons ("HFCs"), e.g., $CH_2FCF_3$ ("HFC-134a"), are being used or have been proposed as CFC substitutes (and HFC-134a has been characterized as being more "ozone friendly"—see U.S. Pat. No. 5,118,494 (Schultz et al.)). Hydrochlorofluorocarbons ("HCFCs"), such as $CH_3CCl_2F$ ("HCFC-141b"), as the *C&EN* article, supra, points out, are CFC substitutes, but although they are not nearly as damaging, these substitutes do carry ozone-depleting chlorine into the stratosphere. Another proposed substitute is the simple omega-hydrodifluoromethyl perfluoromethyl ether, $CF_3OCF_2H$—See J. L Adcock et. al., "Fluorinated Ethers—A new Family of Halons," 1991 CFC Conference Proceedings (1991). Another hydro-fluoroalkyl ether (or ether hydride), $F[CF(CF_3)CF_2O]_4CFHCF_3$, made by decarboxylation of the fluorinated 2-alkoxypropionic acid salt, has been tested as a blood emulsion—see *Chem. Pharm. Bull.* 33, 1221 (1985).

U.S. Pat. No. 4,173,654 (Scherer) states that fluorocarbons due to their inertness have found use as electronic coolant or leak testing fluids, and other compounds having good solubility for oxygen have been investigated as artificial blood substitutes. This patent describes certain fluorocarbon "hybrid" materials with metabolically active hydrocarbon moieties, such as, inter alia, $—CH_2—(CH_2)_m—H$. U.S. Pat. No. 4,686,024 (Scherer et al.), which describes certain perfluorocyclic ethers, states that various perfluoro chemicals are disclosed in patents as being suitable as oxygen and carbon dioxide carriers. And International Application published as WO 93/11868 (Kaufman et al.) describes certain chlorofluorochemicals and emulsions thereof as useful in various oxygen transport applications, e.g., as oxygen transfer agents or "artificial bloods."

There are a number of other patents describing various fluorocarbon ethers or polyethers. U.S. Pat. No. 3,342,875 (Selman et al.) describes certain "hydrogen modified fluorocarbon ethers" (or "hydrogen capped polyethers") made, inter alia, by pyrolysis of a hydrogen-containing derivative of an ether, such as the fluorocarbon ether acid or the ammonium salt, which ether is obtained by the polymerization of fluorocarbon. epoxides. British Patent Specification 1,194,431 (Montecatini Edison S.P.A.) describes certain perfluorinated ethers and polyether derivatives having the general formula $$CF_3—O—(C_3F_6O)_M—(CF_2O)_N—(CF(CF_3)—O)_L—CF_2X$$

where, inter alia, each subscript M, N, and L is zero or a whole number from 1 to 99, and X is a hydrogen atom or —COOMe wherein Me is an equivalent of an alkali or alkaline earth metal, an examples of which is pentafluorodimethyl ether, $CF_3—O—CF_2H$.

U.S. Pat. No. 3,597,359 (Smith) describes certain perfluoroalkylene ether-containing compound represented by the formula

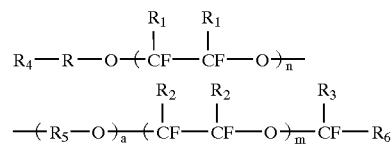

wherein, inter alia, R is alkylene, alkoxyalkylene, or perfluoroalkylene, $R_1$ is fluorine or trifluoromethyl provided not more than one $R_1$ is trifluoromethyl, $R_2$ is fluorine or trifluoromethyl provided not more than one $R_2$ is trifluoromethyl, $R_3$ is fluorine or trifluoromethyl, $R_4$ is hydrogen or halogen provided that when R is alkylene or alkoxyalkylene $R_4$ is hydrogen, $R_5$ is perfluoroalkylene having at least 2 carbon atoms, $R_6$ is, inter alia hydrogen, trifluoromethyl or perfluoroethyl, a is zero or 1, n and m are whole numbers of 0 to 50, and n+m is 1 to 50.

U.S. Pat. No. 3,962,460 (Croix et al.) describes aliphatic ethers, including those of the formulas

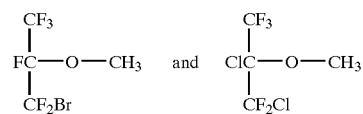

International Patent Application WO 90/01901 (Long) describes certain perfluorocarbon hydrides, such as perfluorooctyl hydride, used in emulsions for carrying oxygen to the tissues of an animal body. European Patent Application Publication No. 0 482 938 A1 (Chambers et al.) describes fluorinated ethers of the formula

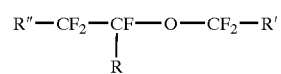

wherein R is hydrogen, fluorine, or alkyl or fluoroalkyl of 1–6 carbon atoms, R' is hydrogen or alkyl or fluoroalkyl of 1 to 6 carbon atoms, and R" is fluorine or alkyl or fluoroalkyl of 1 to 6 carbon atoms.

Other patents describing one or more various fluoroalkoxyalkanoic acids and esters or other derivatives thereof and their preparation are U.S. Pat. No. 2,713,593 (Brice et al.), U.S. Pat. No. 3,214,478 (Milian, Jr.), U.S. Pat. No. 3,393,228 (Braun), U.S. Pat. No. 4,118,421 (Martini), U.S. Pat. No. 4,357,282 (Anderson et al.), U.S. Pat. No. 4,729,856 (Bernonge), U.S. Pat. No. 4,847,427 (Nappa), U.S. Pat. No. 4,940,814 (Schwertfeger), U.S. Pat. No. 4,973,716 (Calini et al.), U.S. Pat. No. 5,053,536 (Bierschenk et al.) U.S. Pat. No. 5,093,432 (Bierschenk et al.), and U.S. Pat. No. 5,118,494 (Schultz et al.) and PCT International Applications Pub. Nos. WO 90/03357 (Moore et al.) and WO 90/06296 (Costello et al.). The aforementioned Brice et al. patent describes fluorocarbons acids made by electrochemical fluorination including an acid having a boiling point of 225° C. and said to be n-$C_8F_{17}OC_2F_4CO_2H$. The aforementioned Nappa, Bierschenk et al., Moore et al., and Costello et al. publications describe the preparation of the fluorinated compounds by direct fluorination of hydrocarbon analog precursors.

In one aspect, this invention provides a normally liquid (i.e., liquid under ambient conditions of temperature and pressure) fluoroalkyl ether compound or a normally liquid composition consisting or consisting essentially of a selected mixture of such compounds, said compound having a saturated perfluoroaliphatic chain of carbon atoms (e.g., 4 to 30) interrupted by one or a plurality (e.g., 2 to 8) of ether (or catenary, i.e., in-chain) oxygen atoms. The chain carbon atom at one end (hereafter called the proximal end) of the chain is bonded to a hydrogen atom (i.e., an omega-hydro substituent, or primary hydrogen atom) and two fluorine atoms, said proximal carbon atom being the carbon atom of a difluoromethyl group or moiety, —$CF_2H$, which is directly bonded to another chain carbon atom, such as that of perfluoroalkylene chain segment, —$C_NF_{2N}$—, or to a said ether-oxygen. The carbon atom at the other end of the chain (the distal end) is part of a distal group selected from the group consisting of a difluoromethyl, a difluorochloromethyl, —$CF_2Cl$, a perfluoroalkyl substituted with a saturated alicyclic moiety, e.g., c-$C_6F_{11}$—, a straight-chain perfluoroalkyl, and a branched chain perfluoroalkyl. In a said compound where said proximal end of the chain terminates in a difluoromethyl group bonded to an ether-oxygen atom, then said straight-chain perfluoroalkyl has at least 6 chain carbon atoms, e.g., 6 to 16 chain carbon atoms, and said branched-chain perfluoroalkyl has at least 4 carbon atoms, e.g., 4 to 16 carbon atoms. Examples of such omega-hydro fluoroalkyl ether compounds are:

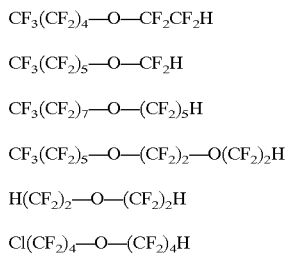

$CF_3(CF_2)_4$—O—$CF_2CF_2H$ $CF_3(CF_2)_5$—O—$CF_2H$ $CF_3(CF_2)_7$—O—$(CF_2)_5H$ $CF_3(CF_2)_5$—O—$(CF_2)_2$—O$(CF_2)_2H$ $H(CF_2)_2$—O—$(CF_2)_2H$ $Cl(CF_2)_4$—O—$(CF_2)_4H$

If a said "selected mixture," i.e., a predetermined mixture of selected omega-hydrofluoroalkyl ether compounds, is desired for a particular use, a said composition of this invention can be made consisting or consisting essentially of a mixture of two or more of said compounds each having a desired discrete, non-random molecular weight, the selected compounds preferably being those having complementary properties, e.g., for imparting improved stability to emulsions where they are incorporated as oxygen carriers in medical applications.

The term "perfluoro," such as in the case of "perfluoroaliphatic," "perfluoroalkylene," or "perfluoroalkyl," means that except as may be otherwise indicated there are no carbon-bonded hydrogen atoms replaceable with fluorine nor any unsaturation.

Omega-hydrofluoroalkyl ethers of this invention are hydrophobic and less oleophobic than the perfluoroalkyl ether analogs, chemically inert, thermally stable, water insoluble, and normally liquid (e.g., at 20° C.), and they can be made in accordance with this invention in high yield, high purity, and with a wide range of molecular weights. The covalent bond between the omega-hydrogen and terminal carbon, i.e., the C—H bond, is generally degradable by atmospheric photo-oxidation, thus making the omega-hydrofluoroalkyl ethers environmentally acceptable or compatible. The omega-hydrofluoroalkyl ether compounds, or the normally liquid composition consisting or consisting essentially thereof, can be used in applications where the aforementioned CFCs, HCFCs or halons have been used, for example, as solvents for precision or metal cleaning of electronic articles such as disks or circuit boards, heat transfer agents, coolants in refrigerator or freezer compressors or air conditioners, blowing agents or cell size regulators in making polyurethane foam insulation, or chemical fire extinguishing agents in streaming applications, total flooding, explosion suppression and inertion, and as carrier solvents for highly fluorinated polyethers used as lubricants for magnetic recording media. Another field of utility for the omega-hydrofluoroalkyl ethers is in emulsions useful in various medical and oxygen transport applications, for example, artificial or synthetic bloods.

The above-described omega-hydrofluoroalkyl ethers of this invention can be prepared by decarboxylation of the corresponding precursor fluoroalkyl ether carboxylic acids and salts thereof or, preferably, the saponifiable alkyl esters thereof. Alternatively, the omega-hydrofluoroalkyl ethers can be prepared by reduction of the corresponding omega-chlorofluoroalkyl ethers (e.g., those described in WO 93/11868, supra). The perfluoroalkyl ether carboxylic acids (and esters) themselves—some of which are believed novel compounds and they and their preparation are other aspects of this invention—can be prepared by direct fluorination of their corresponding hydrocarbon analogs. The omega-hydrofluoroalkyl ethers are essentially pure fluorinated compounds and are useful as such or in the form of a normally liquid composition consisting or consisting essentially of a selected mixture of such compounds. The precursor perfluoroalkyl ether carboxylic acid and ester compounds, like the above-described omega-hydrofluoroalkyl compounds of this invention, have a saturated perfluoroaliphatic chain of a plurality of carbon atoms, said chain likewise being interrupted by one or a plurality of ether oxygen atoms, the proximal end of the chain being connected to a carboxyl group or alkyl ester thereof. This carboxyl group (or salts thereof or its saponifiable alkyl ester) can be decarboxylated, as mentioned above, and thereby replaced by the aforementioned omega-hydro substituent of the resulting omega-hydroalkyl ether of this invention.

The aforementioned novel perfluoroalkyl ether acids and esters can also be converted into various other derivatives, such as their ammonium salts, which have utility as surface active agents useful in modifying the surface tension or interfacial tension of liquids. These compounds are more soluble in aqueous media and other organic solvents than are the corresponding perfluoroalkanoic acid derivatives, and this enhances their utility as surface-active agents. The compounds can conveniently be prepared by direct fluorination of the corresponding hydrocarbon ether acids, or derivatives such as an ester, in high yields as single molecular species.

A class of the normally liquid, omega-hydrofluoroalkyl ether compounds of this invention can be represented by the general formula:

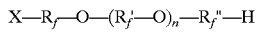   I wherein:

H is a primary hydrogen atom;

X is a fluorine atom, a primary hydrogen atom, or a primary chlorine atom bonded to a difluoromethylene (of $R_f$);

n is a integer of 0 to 7, preferably 0 to 3;

$R_f$, $R_f'$, and $R_f''$ are the same or different perfluoroalkylene (linear or branched) groups, e.g., —$CF_2CF_2$—, which are unsubstituted or substituted with a perfluoro organo group which can contain ether oxygen, for example, $R_f$ can be —$CF_2CF(R_f''')CF_2$— or —$R_f'''CF_2$— where $R_f'''$ is a saturated perfluoroalicyclic group having 4 to 6 ring carbon atoms, such as perfluorocyclohexyl or perfluoro-cyclohexylene;

with the proviso that when X is H or Cl, $R_f$ has 1 to 18, preferably 2 to 18, chain carbon atoms, $R_f'$ has 1 to 12, preferably 2 to 12, chain carbon atoms, and $R_f''$ has 2 to 12 chain carbon atoms;

and with the further proviso that when X is F, then $R_f$ has at least 4, preferably 4 to 18, chain carbon atoms, $R_f'$ has 1 or more, preferably 1 to 12, more preferably 2 to 12, chain carbon atoms, and $R_f''$ has 2 or more, preferably 2 to 12, chain carbon atoms.

A subclass of polyether compounds within the scope of general formula I is represented by the general formula:

X—$R_f$—O—($CF_2CF_2$—O)$_m$—$R_f''$—H   II where m is an integer of 0 to 7, and H, X, $R_f$, and $R_f''$ are as defined for formula I.

Another subclass of compounds within the scope of general formula I is represented by the general formula:

F—$R_f$—O—($R_f'$—O)$_p$—$R_f''$—H   III where p is an integer of 0 to 2 and H, $R_f$, $R_f'$, and $R_f''$ are as defined for formula I, except $R_f$ has 4 to 12 chain carbon atoms, $R_f'$ has 1 to 12 chain carbon atoms, and $R_f''$ has 2 to 12 chain carbon atoms.

Another class of the normally liquid, omega-hydrofluoroalkyl ether compounds of the invention can be represented by the general formula:

wherein:

H is a primary hydrogen atom;

X is a fluorine atom, a primary hydrogen atom, or a primary chlorine atom;

n is an integer of 0 to 7; and $R_f$, $R_f'$, and $R_f''$ are independently selected from the group consisting of linear or branched, unsubstituted perfluoroalkylene groups; linear or branched, perfluoroalkyl- or perfluorocycloalkyl-substituted perfluoroalkylene groups; and linear or branched perfluoroalkylene groups substituted with an ether oxygen-containing moiety;

with the proviso that when X is H or Cl, $R_f$ has 1 to 18 chain carbon atoms and each of $R_f'$ and $R_f''$ independently has 1 to 12 chain carbon atoms;

and with the further proviso that when X is F, then $R_f$ has at least 4 chain carbon atoms and each of $R_f'$ and $R_f''$ independently has 1 or more chain carbon atoms;

and with the still further proviso that when n is zero, then $R_f$ is a perfluorocycloalkyl-substituted perfluoroalkylene group.

A list of representative examples of the omega-hydrofluoroalkyl ether compounds of this invention is as follows.

Table A

1. $CF_3(CF_2)_5$—O—$CF_2H$
2. $CF_3(CF_2)_3$—O—$(CF_2)_2H$
3. c-$C_6F_{11}CF_2$—O—$(CF_2)_2H$
4. $CF_3(CF_2)_3$—O—$CF_2C(CF_3)_2CF_2H$
5. $(CF_3)_2CFCF_2$—O—$CF_2H$
6. $CF_3(CF_2)_4$—O—$(CF_2)_5H$
7. $CF_3(CF_2)_6$—O—$CF_2H$
8. $CF_3(CF_2)_5$—O—$(CF_2)_2H$
9. $CF_3(CF_2)_5$—O—$(CF_2)_3H$
10. $CF_3(CF_2)_6$—O—$(CF_2)_2H$
11. $CF_3(CF_2)_7$—O—$CF_2H$
12. $CF_3(CF_2)_7$—O—$(CF_2)_5H$
13. $CF_3(CF_2)_7$—O—$(CF_2)_6H$
14. $CF_3(CF_2)_5$—O—$(CF_2)_2$—O—$CF_2H$
15. $CF_3(CF_2)_5$—O—$(CF_2)_2$—O—$(CF_2)_2H$
16. H—$(CF_2)_2$—O—$(CF_2)_2H$
17. H—$(CF_2)_4$—O—$(CF_2)_4H$
18. H—$(CF_2)_2$—O—$(CF_2)_2$—O—$(CF_2)_2H$
19. H—$CF_2$—O—$CF_2C(CF_3)_2CF_2$—O—$CF_2H$
20. $Cl(CF_2)_4$—O—$(CF_2)_4H$
21. $H(CF_2)_2OCF_2C(CF_3)_2CF_2O(CF_2)_2H$
22. $C_8F_{17}OCF_2OC_3F_6H$
23. $(CF_3)_3COC_2F_4OCF_2OC_2F_4OCF_2H$

As mentioned above, the omega-hydrofluoroalkyl ether compounds or compositions of this invention can be made by decarboxylation of their corresponding precursor perfluoroalkyl ether carboxylic acids, hydrolyzable carboxylic acid derivatives, or hydrolyzable precursors thereto (some of which are believed novel). A class of such precursor compounds can be represented by the general formula:

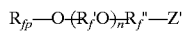   IV wherein $R_{fp}$ is ROC(O)$R_f$ or F—$R_f$, $R_f$ being a perfluoroalkylene group as defined for formula I;

$R_f'$ and $R_f''$ are also perfluoroalkylene groups as defined for formula I;

n is also as defined for formula I; and

Z' is a $CO_2H$, $CO_2R$, COF, COCl, CONR$^1$R$^2$, or —$CF_2OC(O)R_f$, where R is selected from the group consisting of hydrogen, alkyl (such as a lower alkyl group of 1 to 6 carbon atoms), cycloalkyl, fluoroalkyl, and aryl, and where R$^1$ and R$^2$ are independently selected from the group consisting of hydrogen, alkyl, cycloalkyl, and heteroatom-containing cycloalkyl.

In the decarboxylation of the compounds of formula IV, the moiety Z' is replaced by a hydrogen atom.

Subclasses of said ether acids and derivatives thereof, which have other utilities in addition to their use as precursors of the omega-hydro ether compounds of this invention, for example, as surface active agents (or surfactants), as mentioned above, and which are believed novel, can be represented by the general formulas V, VI, VII, VIII and IX below, $$R_{fo}-O-R_{fo}'-Z \qquad V$$

wherein:

$R_{fo}$ is a perfluoroalkyl group (linear or branched) having, for example, 1 to 18 carbon atoms, preferably 1 to 12 carbon atoms, $R_{fo}'$ is a perfluoroalkylene group (linear or branched) having, for example, 2 to 11 carbon atoms, at least one of $R_{fo}$ and $R_{fo}'$ having at least 8 chain carbon atoms; and Z is —COOH, —COOM$_{1/v}$, —COONH$_4$, —COOR, —CH$_2$OH, —COF, —COCl, —CR, —CONRR, —CH$_2$NH$_2$, —CH$_2$NCO, —CN, —CH$_2$OSO$_2$R, —CH$_2$OCOR, —CH$_2$OCOCR═CH$_2$, —CONH(CH$_2$)$_m$Si(OR)$_3$, or —CH$_2$O(CH$_2$)$_m$Si(OR)$_3$, where M is an ammonium radical or a metal atom having a valence "v" of 1 to 4, such as Na, K, Ti, or Al, and each R is independently an alkyl (e.g., with 1 to 14 carbon atoms) or cycloalkyl, which groups can be partially or fully fluorinated, or an aryl (e.g., with 6 to 10 ring-carbon atoms), any of which groups can contain heteroatom(s), and m is an integer of 1 to about 11.

$$R_{fq}(O-CF_2CF_2)_aOCF_2-Z \qquad VI$$

wherein:

$R_{fq}$ is a perfluoroalkyl group (linear or branched) having from about 6 to about 18 carbon atoms, preferably 6 to 12 carbon atoms, subscript a is an integer of at least 2, preferably 3 to 7, but when a is 2, then $R_{fq}$ has at least about 8 carbon atoms; and Z is as defined for formula V.

$$R_{fr}-O-CF_2-O-R_{fr}'-Z \qquad VII$$

wherein:

$R_{fr}$ is a perfluoroalkyl group (linear or branched) having, for example, 2 to 18 carbon atoms, preferably 4 to 12 carbon atoms;

$R_{fr}'$ is a perfluoroalkylene group (linear or branched) having, for example, 1 to 11 carbon atoms and preferably 1 to 5 carbon atoms; and Z is as defined for formula V; and the sum of the number of carbon atoms in the groups $R_{fr}$ and $R_{fr}'$ is at least about 7.

$$R_{fs}-O-(CF_2)_b-Z \qquad VIII$$

wherein:

$R_{fs}$ is a perfluoroalkyl group (linear or branched) having, for example, 1 to 18 carbon atoms, preferably 1 to 12 carbon atoms;

b is an integer of at least 3, preferably 3 to 11; and

Z is as defined for formula V.

$$R_{ft}-(O-R_{ft}')_c-O-(CF_2)_d-Z \qquad IX$$

wherein:

$R_{ft}$ is a perfluoroalkyl group (linear or branched) having, for example, 1 to 18 carbon atoms, preferably 1 to 12 carbon atoms;

$R_{ft}'$ is a perfluoroalkylene group (linear or branched) having, for example, 1 to 11 carbon atoms, preferably 2 to 4 carbon atoms;

c is an integer of at least 1, preferably 1 to 4;

d is an integer of 3 or greater, preferably 3 to 9; and

Z is as defined for formula V.

The carboxylic acids of formulas V to IX are useful intermediates for the preparation of many of the other derivatives of formulas V to IX. These derivatives include nonfunctional or functional derivatives such as, for example, carboxylic acids, salts, esters, amides, nitrites, alcohols, acrylates, and vinyl ethers. Various patents describe processes for the preparation of a host of functional derivatives of oxyperfluoroalkylene compounds, i.e., perfluoropolyethers, e.g., see U.S. Pat. No. 3,250,808 (Mitsch et al.) and U.S. Pat. No. 4,094,911 (Moore et al.), which descriptions are incorporated herein. These derivatives have utility for various applications, such as surfactants, elastomers, coatings, lubricants, substances used in the preparation of liquid crystal materials such as those in U.S. Pat. No. 5,262,082 (Janulis et al.), and in the treatment of fibrous substrates to impart oil and water repellency thereto. The ammonium salts of the carboxylic acid derivatives are particularly useful as surfactants.

The carboxylic acid compounds of formula V are normally solid. The carboxylic acid compounds of formulas VI, VII, VIII and IX generally are normally liquid and normally liquid compositions can be made up which consist or consist essentially of selected mixtures of such compounds.

A list of representative examples of fluoroalkylether acids (or derivatives) which can be utilized to prepare omega-hydrofluoroalkyl ethers of this invention is as follows:

Table B

1. $CF_3(CF_2)_7-O-CF_2CO_2H$
2. $CF_3(CF_2)_{11}-O-CF_2CO_2H$
3. $CF_3(CF_2)_6-O-C_2F_4CO_2H$
4. $CF_3(CF_2)_4-O-C_2F_4CO_2H$
5. $CF_3(CF_2)_5-O-C_2F_4CO_2H$
6. $CF_3(CF_2)_8-O-C_2F_4CO_2H$
7. $CF_3(CF_2)_7-O-C_2F_4CO_2H$
8. $CF_3(CF_2)_9-O-C_2F_4CO_2H$
9. $CF_3(CF_2)_{11}-O-C_2F_4CO_2H$
10. $CF_3(CF_2)_5-OC_2F_4O-C_2F_4CO_2H$
11. $C_8F_{17}-O-(CF_2)_5CO_2H$
12. $C_{10}F_{21}-O-(CF_2)_5CO_2H$
13. $CF_3-O-(CF_2)_7CO_2H$
14. $C_2F_5-O-(CF_2)_7CO_2H$
15. $C_3F_7-O-(CF_2)_7CO_2H$
16. $CF_3-O-(CF_2)_9CO_2H$
17. $CF_3-O-(CF_2)_{10}CO_2H$
18. $CF_3(CF_2)_5-O-C_2F_4-O-C_2F_4-O-C_2F_4-O-CF_2CO_2H$
19. $CF_3(CF_2)_7-O-C_2F_4-O-C_2F_4-O-C_2F_4-O-CF_2CO_2H$
20. $CF_3(CF_2)_9-O-C_2F_4-O-C_2F_4-O-C_2F_4-O-CF_2CO_2H$
21. $CF_3(CF_2)_{11}-O-C_2F_4-O-C_2F_4-O-C_2F_4-O-CF_2CO_2H$
22. $CF_3(CF_2)_{11}-(OC_2F_4)_{1-5}-O-CF_2CO_2H$ from Brij$^{tm}$30 acetate
23. $C_6F_{13}OCF_2O(CF_2)_5CO_2H$
24. $CF_3(CF_2)_7-O-CF_2-O-CF_2CO_2H$
25. $CF_3(CF_2)_7-O-CF_2-O-C_3F_6CO_2H$
26. $(CF_3)_3COC_2F_4OCF_2OC_2F_4CO_2H$
27. $C_4F_9-O-(CF_2)_3CO_2H$ 28. $C_5F_{11}$—O—$(CF_2)_3CO_2H$
29. $C_6F_{13}$—O—$(CF_2)_3CO_2H$
30. $C_5F_{11}$—O—$(CF_2)_4CO_2H$
31. $CF_3$—O—$(CF_2)_5CO_2H$
32. $C_4F_9$—O—$(CF_2)_5CO_2H$
33. $C_5F_{11}$—O—$(CF_2)_5CO_2H$
34. $C_4F_9$—O—$C_4F_8$—$O(CF_2)_3CO_2H$
35. $C_6F_{13}$—O—$C_4F_8$—$O(CF_2)_3CO_2H$
36. $C_4F_9$—O—$C_2F_4O$—$C_2F_4O(CF_2)_3CO_2H$
37. $CF_3$—O—$(C_2F_4O)_3$—$(CF_2)_3CO_2H$
38. $C_8F_{17}OCF_2OC_5F_{10}CO_2H$
39. $(CF_3)_3COC_2F_4OCF_2OC_2F_4OCF_2CO_2H$
40. $(CF_3)_2CFCF_2CF_2O(CF_2)_5CO_2H$
41. $CF_3(CF_2)_7OC_2F_4OC_2F_4OCF_2CO_2H$
42. $CF_3(CF_2)_{11}OC_2F_4OC_2F_4OCF_2CO_2H$ The following presents overall schemes of reactions that can be used in the preparation of omega-hydrofluoroalkyl ethers of this invention using general formulas defined above. In these schemes, the illustrated reaction results in the product whose formula is depicted on the succeeding line

Scheme I

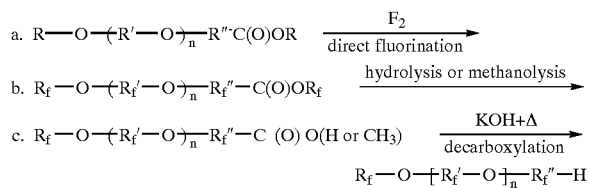

Scheme II

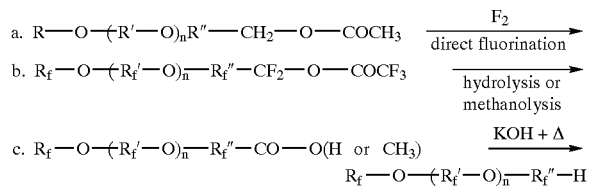

Scheme III

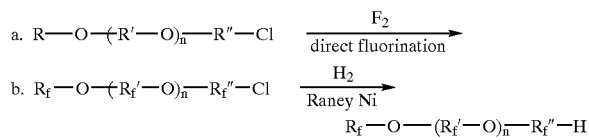

The ether alpha and omega dihydrides, that is, where X in formula I is H, may be prepared by analogous schemes. For example, the following Scheme IV is analogous to Scheme I

Scheme IV

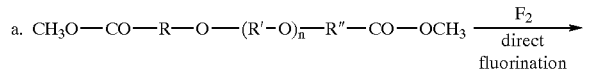

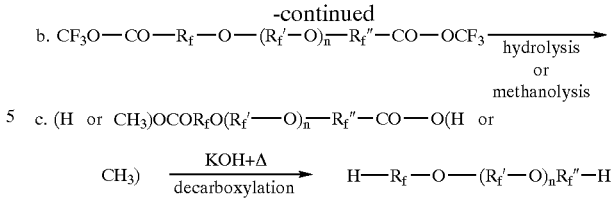

Looking first at Scheme I above, in the direct fluorination, step "a", a fluorinatable precursor ether carboxylic acid ester, e.g., $C_4H_9$—O—$(CH_2)_5COOCH_3$, is directly fluorinated by contact with fluorine gas. (The term "fluorinatable" means that the precursor contains carbon-bonded hydrogen atoms which are replaceable with fluorine and the precursor may contain unsaturation which can be saturated with fluorine.) The resulting fluorinated ether acid ester compound, depicted in step b, can be made with essentially the same number and spatial arrangement of carbon and oxygen atoms as the precursor thereof. If a fluorinated ether acid composition which consists or consists essentially of a selected mixture of fluorinated ether compounds is desired, a selected mixture of the corresponding precursor compounds can be fluorinated or, alternatively, the selected precursor compounds can be separately fluorinated and then blended.

The direct fluorination of the fluorinatable ether precursor can be carried out at temperatures typically used in direct fluorination, e.g., at moderate or near ambient temperatures such as −20° C. to +50° C., using a stoichiometric excess of fluorine gas, which is preferably diluted with an inert gas, such as nitrogen, to minimize or avoid the hazards of pure fluorine gas and to control the amount of heat generated upon contact of the precursor with fluorine. The fluorination is preferably carried out in an oxygen- and and water-free environment and can be carried out in the presence of solid, particulate scavenger, e.g., sodium fluoride, for the hydrogen fluoride by-product generated. Liquid phase direct fluorination can be employed and involves using an inert liquid, such as a fluorocarbon or chlorofluorocarbon liquid, as a reaction medium. Both scavenger and an inert liquid reaction medium can be utilized, if desired. The fluorination is preferably carried out by liquid phase direct fluorination in the absence of hydrogen fluoride scavenger by using a temperature and inert gas flow rate sufficient to volatilize hydrogen fluoride by-product and enable its removal from the fluorination zone as it is generated.

In another aspect, this invention provides a fluorochemical composition containing the fluorinated ether acid or derivative thereof, hereinbefore described, as the sole essential component of the fluorochemical composition.

Although direct fluorination is a substitution method involving the replacement of hydrogen atoms with fluorine, direct fluorination provides higher yields and purer products than do other substitution methods such as the electrochemical fluorination and cobalt trifluoride methods—see, for example, U.S. Pat. No. 5,093,432 (Bierschenk et al.). The purity of the perfluorinated ether acid (or ester) compositions of the invention is further enhanced by the use of single precursor compounds or selected (rather than random) mixtures thereof.

The preferred method of fluorination is the "liquid phase direct fluorination technique," which involves making a very dilute dispersion or, preferably, solution of the precursor(s) in a liquid reaction media, which is relatively inert to fluorine at the fluorination temperatures used, the concentration of fluorinatable starting material thus being relatively low so as to more easily control the reaction temperature. The reaction mixture can also contain or have dispersed therein a hydrogen fluoride scavenger such as sodium fluoride, the scavenger:precursor weight ratio being, for example, from about 0.5:1 to 7:1. The reaction mixture can be vigorously agitated while the fluorine gas is bubbled through it, the fluorine preferably being used in admixture with an inert gas, such as nitrogen, at a concentration of about 5 to 50 volume %, more preferably about 10 to 25 volume %, and being maintained in stoichiometric excess throughout the fluorination, e.g., up to 15 to 40%, or higher, depending on the particular starting material and the efficiency of the equipment used, such as the reactor agitation. Yields generally in the range of about 30–77 mole %, and, with experience, as high as 65 to about 85 mole %, of the perfluorinated product may be achieved by this method.

Suitable liquids useful as reaction media for the liquid phase direct fluorination technique are chlorofluorocarbons such as Freon™ 11 fluorotrichloromethane; chlorofluoroethers; Fluorinert™ electronic liquids FC-75, FC-72, and FC-40; perfluoroalkanes such as perfluoropentane and perfluorodecalin; perfluoropolyethers; and perfluoroacetals. Mixtures of such liquids can be used, e.g., to get good dispersion of precursor and intermediate reaction products. The reaction media are conveniently used at atmospheric pressure. Lower molecular weight members of the above classes of reaction media can also be used, but elevated pressures are then required to provide a liquid phase.

The liquid phase direct fluorination reaction is generally carried out at a temperature between about −10° C. to +50° C., preferably between about −10° C. to 0° C. if a hydrogen fluoride scavenger is used, and, if such a scavenger is not used, between about 0° C. to 150° C., preferably about 0° C. to 50° C., most preferably about 10° C. to 30° C., the temperature being sufficient to volatilize the hydrogen fluoride by-product and, with the aid of the inert gas, flowing at a sufficient rate, cause the purging of the by-product from the fluorination reactor as it is generated. At these temperatures, the liquids utilized as reaction media do not react appreciably with the diluted fluorine and are essentially inert. The reaction medium and other organic substances may to some extent be present in the gaseous reactor effluent, and a condenser may be used to condense the gaseous reaction medium and such substances in the effluent and permit the condensate to return to the reactor. The condenser can be operated so as to minimize or prevent the return to the reactor of hydrogen fluoride by-product (which could have an adverse effect on yield of product if allowed to remain in the reactor during fluorination). The return of the hydrogen fluoride can be minimized or prevented by selective condensation of the organic materials while allowing the hydrogen fluoride to pass through the condenser, or by total condensation of both hydrogen fluoride and the organic materials into a separate vessel and followed, if desired, by separation of the hydrogen fluoride as the upper liquid phase and the return of the lower liquid phase.

The liquid phase fluorination reaction may be carried out in a batch mode, in which all of the precursor is added to the liquid prior to fluorination to provide a precursor concentration of up to about 10% by weight, and the fluorine-containing gas is then bubbled through the precursor-containing liquid. The reaction can also be carried out in a semi-continuous mode, in which the precursor is continuously pumped or otherwise fed neat, or as a diluted solution or dispersion, in a suitable liquid of the type used as a reaction medium, into the reactor, e.g., at a rate of about 1 to 3 g/hr into 400 mL of liquid reaction mixture, as fluorine is bubbled through, e.g., at a fluorine flow rate of about 40 to 120 mL/min and an inert gas flow rate of about 150 to 600 mL/min. The fluorination can also be carried out in a continuous manner, in which the precursor (either neat or dissolved or dispersed in a suitable liquid of the type used as a reaction medium) is continuously pumped or otherwise fed into the reactor containing the reaction medium as the fluorine-containing gas is introduced, as described above, and the stream of unreacted fluorine, hydrogen fluoride gas, and inert carrier gas is continuously removed from the reactor, as is a stream of liquid comprising perfluorinated product, incompletely fluorinated precursor, and inert liquid reaction medium, and the necessary separations are made to recover the fluoroalkyl ether composition. If desired, the unreacted fluorine and the incompletely fluorinated precursor can be recycled. The amount of inert liquid medium in the reactor can be maintained at a constant level by addition of recycled or fresh liquid.

Due to the extremely high exothermicity of the fluorination reaction, a cooled liquid or ice bath is generally employed in order that acceptable rates of reaction may be achieved. When the reaction is complete, the reactor is purged of fluorine and the reactor contents are removed. Where the fluorination is carried out by the liquid phase fluorination technique in the presence of a hydrogen fluoride scavenger, the spent scavenger can be separated by filtration or decantation from the liquid reactor contents and the latter then distilled to separate the reaction medium from the crude product. Where the fluorination is carried out by the liquid phase fluorination technique without using the scavenger, the reaction product mixture can be distilled to recover the product.

Useful representative precursor fluorinatable ether acid esters which can be used to prepare the omega-hydrofluoroalkyl ethers of this invention are the hydrocarbon counterparts of the structures listed in Table A above, except that instead of the terminal hydrogen atom the structures of the esters terminate with -Z' (where Z' is as defined for formula IV) or —CH$_2$OC(O)R (as shown in Scheme II supra) and that the precursors can contain unsaturation.

Representative examples of the fluoroether acids of or used in this invention include the perfluorinated (i.e., having essentially all hydrogens replaced with fluorine) counterparts of the precursor fluorinatable acid esters described above. When the precursors have unsaturation, the corresponding fluorinated ether acids are saturated.

As pointed out above, the fluoroether acids and derivatives can be used as precursors in the preparation of the omega-hydrofluoroalkyl ethers and they are also useful, for example, as surfactants.

The above-described fluoroether acids or the esters thereof, e.g., alkyl esters such as the methyl ester, can be converted by a decarboxylation process to the omega-hydrofluoroalkyl ethers of this invention. In one such process, a solution of KOH in ethylene glycol is prepared and the fluoroether acid or ester precursor is added thereto (neat or as a solution in an inert solvent liquid such as a perfluorinated liquid), preferably dropwise with stirring at ambient or room temperature. The resulting mixture can then be heated slowly, for example, to 190° C., during which time the methanol (from the saponification of a methyl ester), water (from neutralization of an acid), and decarboxylated product are distilled. The omega-hydrofluoroalkyl ethers of the invention are surprisingly stable under such harsh basic conditions. An inert solvent liquid, if used, can be removed, for example, at low temperature under vacuum after neutralization. The resulting distillate, comprising the omega-hydrofluoroalkyl ether product, can be washed with water, dried with silica gel or magnesium sulfate, and then distilled to purify the product. If desired, the hydrofluoroalkyl ether product can be refluxed with a solution of potassium permanganate in acetone to remove easily-oxidized impurities. The yields of the ether product are generally high and the product generally will be quite pure and consist or consist essentially of the desired omega-hydrofluoroalkyl ether.

The omega-hydrofluoroalkyl ether compositions are non-toxic and capable of dissolving and transporting oxygen and are therefore potentially useful as blood substitutes which can be employed invasively in the treatment of trauma, vascular obstructions, as adjuvants to cancer radiation treatment or chemotherapy, and as imaging contrast agents. For such uses, emulsions of the compositions can be prepared by methods such as those described, for example, in U.S. Pat. No. 3,911,138 (Clark) and U.S. Pat. No. 5,077,036 (Long) and the PCT International Application published as WO 93/11868 (Kaufman et al.), which descriptions are incorporated herein by reference. The omega-hydrofluoroalkyl ether compositions are also useful as solvents for cleaning and drying applications such as those described in U.S. Pat. No. 5,125,089 (Flynn et al.), U.S. Pat. No. 3,903,012 (Brandreth), and U.S. Pat. No. 4,169,807 (Zuber). Minor amounts of optional components, e.g., surfactants, may be added to the fluoroether compositions to impart particular desired properties for particular uses. The ether compositions are also useful as heat transfer agents or coolants in refrigerator or freezer compressors or air conditioners, blowing agents or cell size regulators in making polyurethane foam insulation, or chemical fire extinguishing agents in streaming applications, total flooding, explosion suppression and inertion, and as carrier solvents for highly fluorinated polyethers used as lubricants for magnetic recording media.

In using the omega-hydrofluoroalkyl ether compositions of this invention for the drying of or displacing water from the surface of articles, such as circuit boards, the processes of drying or water displacement described in U.S. Pat. No. 5,125,978 (Flynn et al.) can be used. Broadly, such process comprises contacting the surface of an article with a liquid composition comprising the ether composition of this invention, preferably in admixture with a non-ionic fluoro-aliphatic surface active agent. The wet article is immersed in the liquid composition and agitated therein, the displaced water is separated from the liquid composition, and the resulting water-free article is removed from the liquid composition. Further description of the process and the articles which can be treated are found in said U.S. Pat. No. 5,125,978, which description is incorporated herein.

In using the ether composition of this invention as a heat transfer liquid in vapor phase soldering, the process described in U.S. Pat. No. 5,104,034 (Hansen) can be used, which description is incorporated herein. Briefly, such process comprises immersing the component to be soldered in a body of vapor comprising the ether composition of this invention to melt the solder. In carrying out such a process, a liquid pool of the ether composition of this invention can be heated to boiling in a tank to form a saturated vapor in the space between the boiling liquid and a condensing means, a workpiece to be soldered is immersed in the vapor whereby the vapor is condensed on the surface of the workpiece so as to melt and reflow the solder, and the soldered workpiece is then removed from the space containing the vapor.

In using the ether composition of this invention as a blowing agent in making plastic foam, such as foamed polyurethane, the process reactants, and reaction conditions described in U.S. Pat. No. 5,210,106 (Dams et al.) can be used, which description is incorporated herein. In carrying out such process, organic polyisocyanate and high molecular weight compound with at least 2 reactive hydrogen atoms, such as a polyol, are admixed in the presence of a blowing agent mixture comprising an ether composition of this invention, catalyst, and a surfactant.

This invention is further illustrated by the following examples, but the particular materials and amounts thereof recited in these examples, as well as other conditions and details, should not be construed to unduly limit this invention.

EXAMPLE 1

Preparation of $C_8F_{17}$—O—$C_2F_4H$ from $C_8F_{17}$—O—$C_2F_4CO_2CH_3$

The organic starting material, $C_8H_{17}$—O—$C_2H_4CO_2CH_3$, was prepared by base-catalyzed Michael addition of n-octanol to acrylonitrile, followed by acid-catalyzed methanolysis. The methyl ester was directly fluorinated with $F_2$ to produce the fluorinated ester, $C_8F_{17}$—O—$C_2F_2CO_2CF_3$. This fluorination was carried out in a 2-liter, jacketed reactor vessel of Monel™ metal equipped with a magnetic drive agitator, gas feed line, organic reactant feed line, and a reflux condenser. The gas feed line was 0.3 cm diameter tube reaching to a point below the bottom impeller of the agitator. The feed line was a 0.15 cm diameter tube connected to a syringe pump. The reflux condenser consisted of about 6-meters of two coiled concentric tubes, the inner tube having a 1.27 cm diameter and the outer tube having a 2.54 cm diameter. Gases from the reactor were cooled in the inner tube by refrigerant, ethylene glycol-water, flowing in the annulus between the two tubes. The reactor was charged with about 1.8 liters of Freon™ 113 chlorofluorocarbon and purged with 650 mL/min of nitrogen for 20 minutes. The gas stream was then changed to a mixture of 310 mL/min fluorine and 1100. mL/min nitrogen. After about 12 minutes, 100 g of $C_8H_{17}$—O—$C_2H_4$—$CO_2CH_3$, diluted to 260 mL with Freon™ 113 chlorofluorocarbon, was fed to the reactor at a rate of 13 mL/hr (5 g/hr feed rate). The reactor contents were maintained at about 16–18° C. throughout the fluorination. The condenser temperature was about −22° C. The fluorine flow was continued for ten minutes after complete addition of the organic feed. The reactor was then purged with nitrogen for one hour. The Freon™ 113 solution of the crude perfluorinated ester was treated with 150 mL of 14% $BF_3$ in methanol and agitated vigorously for 24 hrs. The mixture was washed with water, dried over $MgSO_4$ and distilled (b.p. 40° C./0.2 torr) to yield $C_8F_{17}$—O—$C_2F_4$—$CO_2CH_3$ (47% yield). For purposes of decarboxylation, 39 g of 85% KOH was dissolved in approximately 300 mL of ethylene glycol and the above-described fluorinated methyl ester was added dropwise with stirring to the KOH solution at room temperature. Upon complete addition, the reaction mixture had a pH of 8 to 9. The mixture was heated slowly with stirring and the product of decarboxylation, $C_8F_{17}$—O—$C_2F_4H$, was distilled along with methanol from saponification of the methyl ester, water from the KOH and a small amount of ethylene glycol. When the reaction mixture temperature reached 170° C., the heating was stopped. The lower fluorochemical phase of the distillate was separated, washed with water, dried and distilled through a three-plate Snyder column. The main fraction, boiling at 146–150° C., yielded 122 g of product.

Gas chromatography and mass spectrometry (GC/MS) of a sample of the product showed the sample to be 94% pure and confirmed the structure as $C_8F_{17}$—O—$C_2F_2H$.

EXAMPLE 2

Preparation of $C_8F_{17}$—O—$C_2F_4H$ from $C_8F_{17}$—O—$C_2F_4CO_2H$ $C_8H_{17}$—O—$C_2H_4CO_2CH_3$ was prepared by base-catalyzed Michael addition of n-octanol to acrylonitrile, followed by acid-catalyzed methanolysis. This carboxylic acid ester was directly fluorinated by essentially the same fluorination procedure described in Example 1 to produce the corresponding ether acid, $C_8F_{17}$—O—$C_2F_4COOH$ upon hydrolysis. Differential scanning calorimetry revealed multiple transitions, which is characteristic of polymorphism.

A solution of 116 g of 85% KOH in 800 mL of ethylene glycol was prepared in a 3 L round-bottom flask. 1000 g of the $C_8F_{17}OC_2F_4$—$CO_2H$ was added dropwise to the stirred KOH solution. Upon complete addition, an additional 10 g of KOH was added and the mixture heated. The fluorochemical product of decarboxylation was distilled together with a small amount of water from the neutralization of the acid. The lower fluorochemical phase of the distillate was separated, washed with salt water, dried over $Na_2SO_4$ and distilled as in Example 1 to yield 817 g of $C_8F_{17}$—O—$C_2F_4H$.

EXAMPLE 3

Preparation of $C_7F_{15}$—O—$C_2F_4H$ from $C_7F_{15}$—O—$C_2F_4CO_2CH_3$ $C_7H_{15}$—O—$C_2H_4CO_2CH_3$ was prepared by base-catalyzed Michael addition of n-heptanol to acrylonitrile, followed by acid-catalyzed methanolysis. 550 g of the corresponding-methyl ester, $C_7F_{15}$—O—$C_2F_4COOCH_3$, (prepared by essentially the same fluorination and methanolysis procedures of Example 1), was added dropwise to a solution of 166.6 g of KOH in approximately 880 mL of ethylene glycol. The fluorochemical product was recovered essentially as in Example 1 to yield 440 g which was distilled through a six-plate Snyder column and the fraction boiling from 130 to 131° C. was collected (340 g). This fraction was combined with 8.5 g of $KMnO_4$ and approximately 350 g of acetone and heated to reflux. After four hours, an additional 5 g of $KMnO_4$ was added and the resulting mixture was heated for an additional 3 hours. The mixture was filtered, the filter cake washed with acetone, and water was added to the filtrate causing a lower fluorochemical phase to form which was then washed with water, followed by conc. $H_2SO_4$, again with water, and then filtered through silica. $^1H$ NMR and $^{19}F$ NMR confirmed the reaction product to have the desired structure, $C_7F_{15}$—O—$C_2F_2H$. Gas-liquid chromatography of a sample showed it to be 98.7% pure.

EXAMPLE 4

Preparation of $C_6F_{13}$—O—$C_2F_4$—O—$CF_2H$ from $C_6F_{13}$—O—$C_2F_4$—$OCF_2CO_2CH_3$ The starting material, $C_6H_{13}$—O—$C_2H_4$—O—$C_2H_4$—O—$COCH_3$, was prepared by acetylation of hexyloxyethanol with acetyl chloride. The acetate was then converted to $C_6F_{13}$—O—$C_2F_4$—$OCF_2CO_2CH_3$ by essentially the same fluorination and methanolysis procedures of Example 1. 548 g of this fluorochemical was combined with 144.2 g of KOH in 600 g of ethylene glycol. The resulting mixture was heated, distilled and the product, $C_6F_{13}$—O—$C_2F_4$—$OCF_2H$, was recovered as in Example 1. Total yield was 433 g. The product was again distilled (b.p 131° C.) through a 12-inch (30.5 cm) perforated-plate column at atmospheric pressure. The structure of the product was confirmed by $^1H$ and $^{19}F$ NMR as $C_6F_{13}$—O—$C_2F_4$—$OCF_2H$. GC/MS revealed a sample of it to be 99.6% pure.

EXAMPLE 5

Preparation of $C_8F_{17}$—O—$CF_2H$ from $C_8F_{17}$—O—$CF_2$—$CO_2CH_3$ $C_8H_{17}$—O—$C_2H_4$—O—$(CO)CF_3$ was prepared by acetylation of octyloxyethanol with trifluoroacetic anhydride. 100 g of the trifluoroacetate was directly fluorinated by essentially the same fluorination procedures of Example 1 and the fluorination product was quenched with a solution of $BF_3$ in methanol to yield crude $C_8F_{17}$—O—$CF_2$—$CO_2CH_3$, which was further purified by distillation, b. 92–97° C. @20 torr.

A 58 g sample of the latter methyl ester was decarboxylated using 10.8 grams of KOH in ethylene glycol and the product, $C_8F_{17}$—O—$CF_2H$, was recovered as in Example 1. The structure of the product was confirmed by $^{19}F$ NMR. GLC revealed the product to be 99.6% pure, b. 134–136° C.

EXAMPLE 6

Preparation of $C_4F_9$—O—$C_2F_4H$ from $C_4F_9$—O—$C_2F_4$—$CO_2CH_3$

The methyl ester, $C_4H_9$—O—$C_2H_4$—$CO_2CH_3$, was prepared by base-catalyzed Michael addition of n-butanol to acrylonitrile, followed by acid-catalyzed methanolysis. The methyl ester was then converted to the corresponding fluorinated methyl ester, $C_4F_9$—O—$CF_2CF_2$—$CO_2CH_3$, by essentially the same fluorination and methanolysis procedures described in Example 1.

1160 g of the latter methyl ester was added dropwise with stirring to 3103 g of ethylene glycol and 129.5 g of NaOH. The product was distilled (b.p. 83° C.) and treated with $KMnO_4$/acetone, and worked up as in Example 3. The structure of the purified compound, $C_4F_9$—O—$CF_2CF_2H$, was confirmed by $^1H$ and $^{19}F$ NMR and GC/MS.

A sample of this compound was evaluated for use in precision cleaning applications by measuring the solubilities of selected hydrocarbon solvents in the sample. High solubility would indicate improved performance as a cleaning agent relative to perfluorocarbon solvents The following hydrocarbon solvents were found to be soluble in amounts up to 50% by weight with the ether hydride: hexane, heptane, toluene, acetone, 2-butanone, 4-methyl-2-pentanone, ethyl acetate, methanol, ethanol, isopropanol, dimethyl formamide, trans-1,2-dichloroethylene and isopropyl ether. o-Xylene was found to be soluble to 19% by weight. Chloroform was found to be soluble to 45% by weight. Ethylene glycol was found to be soluble to less than 15% by weight and a light hydrocarbon oil was found to be soluble to less than 0.05% by weight.

A sample of the compound was also evaluated for use in spot-free drying applications such as taught in U.S. Pat. No. 5,125,978 (Flynn et al.). A water displacement composition was prepared by dissolving 0.2% by weight of $C_4F_9OC_2F_4OCF_2CONHC_2H_4OH$ in $C_4F_9$—O—$C_2F_4H$. The solution was heated to 45° C. in an ultrasonic bath. Using the procedure described in U.S. Pat. No. 5,125,978, test coupons of glass and stainless steel were wetted with water and subsequently immersed into this solution with ultrasonic agitation. All water was displaced within 60 seconds.

A sample of this compound was also evaluated for use as a rinse agent in co-solvent cleaning applications. (Such cleaning applications are taught, for example, in International Patent Publication No. WO 92/22678 (Petroferm Inc.). Organic esters such as methyl decanoate have found utility as solvating agents in two-phase cleaning applications using perfluorohexane as the carrier liquid and rinse agent.) Methyl decanoate and $C_4F_9OC_2F_4H$ were placed in separate containers and heated to 50° C. in an ultrasonic bath. A 50 mm×25 mm×1.5 mm aluminum coupon was contaminated with 0.0831 g of a light hydrocarbon oil. The contaminated coupon was first immersed in the methyl decanoate for about 60 seconds and then immersed in the $C_4F_9OC_2F_4H$ for about 60 seconds. The $C_4F_9OC_2F_4H$ rinsed 100 percent (as determined by weight difference) of the oil and the methyl decanoate from the coupon. Under the same conditions, perfluorohexane removed only 98.5 percent of the oil and methyl decanoate, indicating that $C_4F_9OC_2F_4H$ can be more effective as a carrier liquid and rinse agent than perfluorohexane.

EXAMPLE 7

Preparation of $HCF_2CF_2$—O—$CF_2CF_2$—O—$CF_2CF_2H$ from $CH_3OC(O)C_2F_4$—O—$C_2F_4$—O—$C_2F_4C(O)OCH_3$ The starting material, $CH_3OC(O)C_2H_4$—O—$C_2H_4$—O—$C_2H_4C(O)OCH_3$, was prepared by base-catalyzed Michael addition of ethylene glycol to acrylonitrile, followed by acid-catalyzed methanolysis. The starting material was then fluorinated and methanolysed by essentially the same procedures described in Example 1 to give $CH_3OC(O)C_2F_4$—O—$C_2F_4$—O—$C_2F_4C(O)OCH_3$.

1136 grams of the fluorinated ester was added to a mixture of 305.6 g of KOH in 2665 g of ethylene glycol. The decarboxylation was carried out essentially as described in Example 1, and the crude product distilled after phase separation but without water washing. The distillate still contained methanol which was removed by a wash with concentrated sulfuric acid followed by two water washes to give 695 g of the desired ether hydride product, with a boiling range of 93–94° C.

EXAMPLE 8

Preparation of $C_4F_9$—O—$(CF_2)_5$H from $C_4F_9$—O—$(CF_2)_5$—$CO_2$H 118.2 g (1.0 mol) hexane-1,6-diol, 4.4 g Adogen™ 464 quaternary ammonium salt, 80.0 g (2.0 mol) NaOH, and 250 mL tetrahydrofuran was stirred at reflux. 80 mL $H_2O$ was added to get better mixing. After 20 min more, 137 g (1.0 mol) butyl bromide was added over 0.5 hr, and stirred overnight at reflux. The reaction mixture was quenched in 1 L $H_2O$, and the upper layer was combined with an ether extract of the lower layer, dried over $MgSO_4$, and stripped on a rotary evaporator. Treating the resulting stripped layer (151 g) in 100 mL $CHCl_3$ with 150 mL acetyl chloride added dropwise and subsequently heating at reflux 4 hr and solvent removal gave 225.4 g of liquid. Distillation of the liquid gave 176.0 g (b. 100–104° C./0.9 torr) of distillate. GLC indicated 56% of it to be the desired 6-butoxyhexyl acetate, accompanied by hexanediol diacetate and dibutoxyhexane.

100 g of this mixture was fluorinated essentially as in Example 1. Treatment of the resulting fluorinated product with 30 mL of a 10 weight percent solution of $H_2SO_4$ in $H_2O$ and shaking at room temperature for 2 hours, filtration of solid fluorinated adipic acid, separation of the F-113 layer, drying over $MgSO_4$, and distillation produced a main cut of 73.4 g, b. 116° C./20 torr, 96% pure $C_4F_9$—O—$(CF_2)_5$COOH. The latter was added to a solution of 10.0 g (0.25 mol) NaOH and 100 mL ethylene glycol and the mixture was heated to 120° C., with $C_4F_9$—O$(CF_2)_6$—O—$C_4F_9$ impurity from fluorination collecting in the Dean-Stark trap. On continued heating, gas evolution began and a liquid, $C_4F_9$—O—$(CF_2)_5$H, (44.6 g) collected in the trap, ending by 170° C. The collected liquid was dried over silica gel and distilled on a 4-inch (10.2 cm) Vigreux column to 38.8 g, b.p 131° C. F-nmr confirmed structure, in high purity, to be $C_4F_9$—O—$(CF_2)_5$H.

EXAMPLE 9

Preparation of $C_5F_{11}$—O—$(CF_2)_5$H from $C_5F_{11}$—O—$(CF_2)_5$COOH

In a similar fashion to Example 8, hexanediol was alkylated with n-pentyl bromide, the product was acetylated, and the crude acetate, $C_5H_{11}$—O—$(CH_2)_6OC(O)CH_3$, was distilled (b. 125° C./3 torr) and the distillate was fluorinated essentially by the fluorination procedure of Example 1. The fluorinated ester was hydrolyzed to the corresponding acid. Decarboxylation of the fluorinated acid, $C_5F_{11}O(CF_2)_5$COOH, with NaOH gave 829 g of product. The product was washed with water, dried over $MgSO_4$, and distilled to yield 555 g of $C_5F_{11}$—O—$(CF_2)_5$H, b. 145–149° C.

EXAMPLE 10

Preparation of $C_8F_{17}$—O—$(CF_2)_5$H from $C_8F_{17}$—O—$(CF_2)_5$COOH

In a fashion similar to Example 8, hexanediol was alkylated with n-octyl bromide, the product was acetylated, and the resulting $C_8H_{17}$—O—$(CH_2)_6$—O—$COCH_3$ was directly fluorinated and hydrolyzed as in Example 8 to $C_8F_{17}$—O—$(CF_2)_5$COOH, which was recrystallized from perfluorohexane. The recrystallized acid (37.5 g) was mixed with 4.0 g NaOH and 100 mL ethylene glycol and heated to 185° C. The product was washed with water, and the residual 27.9 g was distilled to give pure $C_8F_{17}$—O—$(CF_2)_5$H, micro b.p. 195° C.

EXAMPLE 11

Preparation of $C_4F_9$—O—$CF_2C(CF_3)_2CF_2H$ from $C_4F_9$—O—$CF_2C(CF_3)_2CF_2Cl$ The alkylation of 2,2-dimethyl-1,3-propanediol with n-butyl bromide carried out essentially as in Example 8 gave the crude mono-alkylated product, which was treated with $SOCl_2$ to give $C_4H_9$—O—$CH_2C(CH_3)_2CH_2Cl$, b. 80–90° C./20–30 torr. This compound was then fluorinated as in Example 1 to give $C_4F_9$—O—$CF_2C(CF_3)_2CF_2Cl$. 20.0 g of the latter chloride was mixed with 5.3 g water-wet Raney Ni and 50 mL of $NH_3$-saturated methanol. The mixture was left shaking on a Parr hydrogenation apparatus for 3 days at about 25° C., with most of the 21 kPa (3 psig) hydrogen pressure drop occurring in the first day. The product was recovered by filtration and quenched in water, yielding 7.9 g with some mechanical loss. $^{19}$F-nmr confirmed the product to be $C_4F_9$—O—$CF_2C(CF_3)_2CF_2H$. A scaleup to 100 g gave 47 g, distilled to b.p 135° C.

EXAMPLE 12

Preparation of H(CF$_2$)$_4$—O—(CF$_2$)$_4$H from Cl(CF$_2$)$_4$—O—(CF$_2$)$_4$Cl Cl—(CH$_2$)$_4$—O—(CH$_2$)$_4$—Cl was fluorinated as in Example 1 to provide Cl(CF$_2$)$_4$—O—(CF$_2$)$_4$Cl. A mixture of 30.3 g Cl(CF$_2$)$_4$—O—(CF$_2$)$_4$Cl, 11.3 g fresh water-wet Raney Ni, and 200 mL methanol was purged for several minutes with NH$_3$ and pressurized with 310 kPa (45 psig) hydrogen on a Parr hydrogenation apparatus at about 25° C. After 17 hr, pressure had dropped to 255 kPa (37 psig) and the mixture had become acidic, with glass etching noted. More ammonia was added and the reduction was continued, dropping another 62 kPa (9 psig). The reaction product was filtered and quenched in water to give 15.4 g of lower phase, 68% pure product confirmed by GLC to be H(CF$_2$)$_4$—O—(CF$_2$)$_4$H. Distillation yielded 27.0 g, b. 121–124° C., 87% pure.

EXAMPLE 13

Preparation of H(CF$_2$)$_4$—O—(CF$_2$)$_4$H and Cl(CF$_2$)$_4$—O—(CF$_2$)$_4$H from Cl(CF$_2$)$_4$—O—(CF$_2$)$_4$Cl A mixture of 50.0 g Cl(CF$_2$)$_4$—O—(CF$_2$)$_4$Cl and 30 g Zn in butanol was stirred at 110° C. for 2 days. GLC of a sample of the resulting reaction product indicated partial conversion. 21 g more Zn was added and the mixture was heated one more day. Filtration and quenching of the resulting material in water gave 27.0 g of a colorless liquid. The product was 35% of H(CF$_2$)$_4$—O—(CF$_2$)$_4$H, 42% mono hydride, and 16% unreduced dichloride.

EXAMPLE 14

Preparation of C$_6$F$_{13}$—O—CF$_2$CF$_2$H from C$_6$F$_{13}$—O—C$_2$F$_4$CO$_2$H The starting material, C$_6$H$_{13}$—O—C$_2$H$_4$—CO$_2$CH$_3$, was prepared by the Michael addition of hexanol to acrylonitrile followed by acid-catalyzed esterification with methanol. The resulting ester was then fluorinated and hydrolyzed to give the C$_6$F$_{13}$—O—C$_2$F$_4$CO$_2$H.

500 g of the acid C$_6$F$_{13}$—O—C$_2$F$_4$CO$_2$H, was added slowly to a solution of 68.7 g KOH in 700 g ethylene glycol. At the end of the addition, an additional 5 g of KOH was added to the homogeneous solution to bring the pH to 9. The decarboxylation was carried out as in Example 1 and subsequently distilled, producing 327 g of product, b. 104–107° C. The product was treated with potassium permanganate essentially as in Example 3, GC/MS, $^{19}$F nmr, $^1$H nmr and IR confirmed structure of the product as C$_6$F$_{13}$—O—CF$_2$CF$_2$H.

EXAMPLE 15

Preparation of C$_6$F$_{13}$—O—CF$_2$H from C$_6$F$_{13}$—O—CF$_2$CO$_2$CH$_3$

The starting material, C$_6$H$_{13}$—O—C$_2$H$_4$OC(O)CH$_3$, prepared by acetylation of ethylene glycol monohexyl ether, was fluorinated and decarboxylated by essentially the procedures of Example 1 to give 146 g of C$_6$F$_{13}$—O—CF$_2$H (b. 92–96° C.).

EXAMPLE 16

Preparation of CF$_3$CF(CF$_3$)CF$_2$—O—CF$_2$H from CF$_3$CF(CF$_3$)CF$_2$—O—CF$_2$CO$_2$CH$_3$ The starting material, CH$_3$CH(CH$_3$)CH$_2$—O—CH$_2$CH$_2$—OC(O)CH$_3$, was prepared by acetylation of ethylene glycol monoisobutyl ether and conversion by essentially the fluorination and methanolysis procedures of Example 1 to give the methyl ester, CF$_3$CF(CF$_3$)CF$_2$—O—CF$_2$CO$_2$CH$_3$, b. 118–120° C.

149 g of the methyl ester was added to 28.6 g of KOH in 700 g of ethylene glycol rapidly dropwise. The decarboxylation was carried out to afford, after distillation, the product cut, 70 g, b. 45–47° C., of 99% purity by GLC. The structure was confirmed by GC/MS, $^1$H nmr, and $^{19}$F nmr analysis as CF$_3$—CF(CF$_3$)CF$_2$—O—CF$_2$H.

EXAMPLE 17

Preparation of C$_4$F$_9$—O—(CF$_2$)$_4$—O—(CF$_2$)$_3$H from C$_4$F$_9$—O—(CF$_2$)$_4$—O—(CF$_2$)$_3$COOCH$_3$ The starting material, C$_4$H$_9$—O—C$_4$H$_8$—O—(CH$_2$)$_3$CH$_2$OCOCH$_3$, was directly fluorinated and methanolysed essentially by the procedures of Example 1 to produce C$_4$F$_9$—O—C$_4$F$_8$—O—(CF$_2$)$_3$CO$_2$CH$_3$. 56 g of the latter was added rapidly to a solution of 5.6 g KOH in 250 ml of ethylene glycol. The decarboxylation was carried out and the product phase separated, washed once with brine, and distilled to yield 36.6 g of product (b.p. 155–158° C.) of GLC purity 100%. GC/MS, $^1$H, and $^{19}$F nmr analysis confirmed the product to be C$_4$F$_9$—O—(CF$_2$)$_4$—O—(CF$_2$)$_3$H.

EXAMPLE 18

Preparation of (C$_2$F$_5$)$_2$CFCF$_2$—O—C$_2$F$_4$H from (C$_2$F$_5$)$_2$CFCF$_2$—O—CF$_2$CF$_2$—C(O)OCH$_3$ Starting material, (C$_2$H$_5$)$_2$CHCH$_2$—O—CH$_2$CH$_2$C(O)OCH$_3$, prepared by the Michael addition of 2-ethylbutanol to acrylonitrile followed by acid-catalyzed esterification with methanol, was fluorinated and methanolysed essentially by the procedures of Example 1 to give (C$_2$F$_5$)$_2$CFCF$_2$—O—CF$_2$CF$_2$—C(O)OCH$_3$, b.p. 159° C., the direct fluorination yield, based on the methyl ester starting material being 88%.

The decarboxylation was carried out essentially as in Example 1 and the product distilled at 108–110° C. to yield 145 g, the IR analysis of which was consistent with the structure (C$_2$F$_5$)$_2$CFCF$_2$—O—CF$_2$CF$_2$H.

EXAMPLE 19

Preparation of c-C$_6$F$_{11}$CF$_2$—O—C$_2$F$_4$H from c-C$_6$F$_{11}$CF$_2$—O—C$_2$F$_4$C(O)OCH$_3$ The starting material, c-C$_6$H$_{11}$CH$_2$—O—C$_2$H$_4$C(O)OCH$_3$, prepared by the reaction of cyclohexylmethanol with acrylonitrile followed by acid-catalyzed esterification with methanol, was then fluorinated and methanolysed with BF$_3$ in methanol by essentially the procedures of Example 1 to give a 65% yield (based on the fluorination) of c-C$_6$F$_{11}$CF$_2$—O—C$_2$F$_4$C(O)OCH$_3$.

224 g of the latter fluorinated ester was added to a solution of 28.2 g of 85% KOH and 466 g ethylene glycol held at 60° C. The resulting mixture was then heated to 100° C. and its pH adjusted to a pH greater than 7 by the addition of 5 g of 45 wt % aqueous KOH. Decarboxylation was carried out by distillation of the resulting mixture. The lower fluorochemical phase of the resulting distillate was separated therefrom, washed with an equal volume of water, and distilled at 123–126° C. to give 155 g of a product (99.7% purity). The product was treated with KMnO$_4$ in acetone to give c-C$_6$F$_{11}$CF$_2$—O—C$_2$F$_4$H.

EXAMPLE 20

Preparation of C$_4$F$_9$—O—C$_2$F$_4$—O—C$_3$F$_6$H from C$_4$F$_9$—O—C$_2$F$_4$—O—C$_3$F$_6$C(O)OCH$_3$ C$_4$H$_9$—O—C$_2$H$_4$—O—C$_4$H$_8$OC(O)CH$_3$ was fluorinated and methanolysed by essentially the procedure of Example 1. The resulting product, $C_4F_9$—O—$C_2F_4$—O—$C_3F_6C(O)$ $OCH_3$, in the amount of 419 g was rapidly added dropwise to a mixture of 49.4 g KOH in 800 g ethylene glycol. The resulting mixture was then heated slowly to a final flask temperature of 190° C. During such heating, methanol from the saponification of the ester, water, and $C_4F_9$—O—$C_2F_4$—O—$C_3F_6H$ distilled from the reaction mixture. Water was added to the distillate and the lower, fluorochemical phase (355 g) was separated and distilled (b. 120–122° C.) to provide 308 g $C_4F_9$—O—$C_2F_4$—O$C_3F_6H$ (82% yield).

EXAMPLE 21

Preparation of $C_6F_{13}$—O—$C_4F_8$—H from $C_6F_{13}$—O—$C_4F_8$—$CO_2CH_3$

The starting material, $C_6H_{13}$—O—$C_5H_{10}$—$OC(O)CH_3$, was prepared by monoalkylation of 1,5-pentanediol with hexyl bromide, followed by acetylation with acetyl chloride. This compound was fluorinated and methanolysed by essentially the procedure of Example 1, to give $C_6F_{13}$—O—$C_4F_8$—$CO_2CH_3$, b.p 100° C. @13 torr. This ester was decarboxylated by heating a solution of 200 grams of ester in 250 mL of ethylene glycol with 30 g of KOH until the hydride product distilled. This liquid was washed with water, dried over $MgSO_4$ to give 128 g of $C_6F_{13}$—O—$C_4F_8$—H of 82% purity. This was further purified by distillation using a 12 plate packed glass column, b.p. 146° C. The structure was confirmed by $^{19}F$ NMR.

EXAMPLE 22

Preparation of $C_6F_{13}$—O—$C_3F_6$—H from $C_6F_{13}$—O—$C_3F_6$—$CO_2^-K^+$

The starting material, $C_6H_{13}$—O—$C_4H_8$—$OC(O)CH_3$, was prepared by monoalkylation of 1,4-butanediol with hexyl bromide, followed by acetylation with acetic anhydride. This compound was fluorinated and methanolysed by essentially the procedure of Example 1, to give $C_6F_{13}$—O—$C_3F_6$—$CO_2CH_3$. The methyl ester was saponified using excess KOH, and then dried in a vacuum oven to yield the potassium salt. 575 g of the salt was heated with stirring in 250 mL of ethylene glycol and the product hydride recovered from the distillate, b.p. 129° C. The structure was confirmed by $^{19}F$ NMR.

EXAMPLE 23

Preparation of $C_5F_{11}$—O—$C_4F_8$—H from $C_5F_{11}$—O—$C_4F_8$—$CO_2^-Na^+$ The starting material, $C_5H_{11}$—O—$C_5H_{10}$—O—$C(O)CH_3$ was prepared by monoalkylation of 1,5-pentanediol with pentyl bromide, followed by acetylation with acetyl chloride. This compound was fluorinated and methanolysed by essentially the procedure of Example 1, to give $C_5F_{11}$—O—$C_4F_8$—$CO_2CH_3$. The methyl ester was saponified using excess NaOH, and decarboxylated and distilled essentially as in Example 22. Distillation through a twelve-plate packed glass column gave pure $C_5F_{11}$—O—$C_4F_8$—H, b.p. 125° C. The structure was confirmed by $^{19}F$ NMR.

EXAMPLE 24

Preparation of $C_4F_9$—O—$C_3F_6$—H from $C_4F_9$—O—$C_3F_6$—$CO_2^-Na^+$

The starting material, $C_4H_9$—O—$C_4H_8$—$OC(O)CH_3$, was prepared by monoalkylation of 1,4-butanediol with butyl bromide, followed by acetylation with acetyl chloride. This compound was fluorinated and methanolysed by essentially the procedure of Example 1, to give $C_4F_9$—O—$C_3F_6$—$CO_2CH_3$. This methyl ester was saponified, decarboxylated and the crude hydride recovered as in Example 23, and then further distilled to yield pure $C_4F_9$—O—$C_3F_6$—H, b.p. 90° C. The structure was confirmed by $^{19}F$ NMR.

EXAMPLE 25

Evaluation of Surfactant Activity of Perfluoroether Carboxylic Acids

The surfactant activity of novel perfluoroether carboxylic acids of this invention was measured with a DeNuoy tensiometer after conversion of the acids to the corresponding ammonium salts. The acids were prepared by direct fluorination of their hydrocarbon precursors, followed by hydrolysis. The ammonium salts were prepared by treatment of the acid with excess aqueous ammonia followed by freeze drying. The results are reported in dynes/cm in the following Table C which lists the parent acid (from Table B) of the ammonium salt.

TABLE C

| Parent Acid from Table B | Melting Point(s) of Acid (° C.) | Surface Tension (dynes/cm) Concentration of Ammonium Salt | | | |
|---|---|---|---|---|---|
| | | 50 ppm | 100 ppm | 500 ppm | 1000 ppm |
| 18 | −1 | 24 | 21 | 18 | |
| 2 | | 21 | 24 | | |
| 4 | | 63 | 59 | 39 | 29 |
| 5 | | 33 | 33 | 26 | 22 |
| 7 | 19 | 37 | 26 | 19 | 17 |
| 6 | | 31 | 23 | 18 | 17 |
| 8 | | 33 | 31 | 26 | 24 |
| 9 | | 38 | 24 | 20 | 18 |
| 10 | | 38 | 35 | 24 | 19 |
| 27 | −39 | 67 | 63 | 50 | 43 |
| 29 | −9 | 49 | 43 | 29 | 23 |
| 35 | | 18 | 18 | 16 | 16 |
| 25 | −9 | 19 | 15 | 15 | 14 |
| 30 | | 46 | 43 | 32 | 24 |
| 31 | | 69 | 68 | 48 | 52 |
| 32 | | 63 | 54 | 31 | 21 |
| 33 | | 28 | 21 | 15 | |
| 40 | | 48 | 41 | 23 | 19 |
| 11 | 49, 59 | 18 | 15 | 15 | |
| 14 | | 39 | 31 | 18 | |
| 15 | 16, −27 | 30 | 17 | 17 | |
| 16 | | 24 | 19 | 18 | 17 |
| 17 | 90 | 14 | 15 | 15 | |

EXAMPLE 26

Evaluation of Ethers as Fire Extinguishing Agents

Omega-hydrofluoroalkyl ether compounds of this invention were evaluated as fire extinguishing agents using the National Fire Protection Association 2001 Fire Protection Standard, with a cup burner modified to handle liquid compounds. The results, shown below in Table D, indicate that the compounds could be effective agents for fire extinguishing, explosion suppression, and as flammable atmosphere inerting agents.

TABLE D

| Agent | Extinguishment concentration, vol. % |
|---|---|
| $C_4F_9OC_2F_4H$ | 5.6 |
| $HC_3F_6OC_3F_6H$ | 5.7 |

EXAMPLE 27

Preparation of Foamed Polyurethane

Omega-hydrofluoralkyl ether compounds of this invention were evaluated as blowing agents for foams using the procedures taught in U.S. Pat. No. 5,210,106 (Dams et al.). Component A contained 15.0 parts by weight of PAPI™27, a methylene diphenyldiisocyanate having an isocyanate equivalent of 134.0, available from Dow Chemical. Component B of the foam contained 10.5 parts by weight (pbw) of Voranol™ 360, a polyether polyol with a hydroxyl number of 360 available from Dow Chemical; 0.26 pbw of water; 0.26 pbw of an oligomeric fluorochemical surfactant as described in Example 1 of U.S. Pat. No. 3,787,351; 0.13 pbw of Polycat™ 8, a N,N-dimethylcyclohexylamine catalyst available from Air Products; and 1.87 pbw of $C_4F_9OCF_2CF_2H$ as the blowing agent.

The ingredients of Component B were mixed to obtain an emulsion which was then admixed with Component A and stirred at 2500 rpm for 10 seconds. The cream time of the foam was approximately 10 seconds. Rise time and tack-free time was approximately 2 and 3 minutes respectively. The resulting polyurethane foam was rigid and had a uniform distribution of very fine, closed cells.

EXAMPLE 28

Preparation of $(CF_3)_3COC_2F_4OCF_2OCF_2CO_2CH_3$

The precursor, $(t-C_4H_9OC_2H_4O)_2CH_2$, prepared by alkylation of methylene chloride with t-butoxy ethanol, was fluorinated and methanolysed essentially as in Example 1 to yield $(CF_3)_3COC_2F_4OCF_2OCF_2CO_2CH_3$, having a boiling range 80–82° C. at 18 torr, and whose structure was confirmed by $^{19}F$ NMR.

EXAMPLE 29

Preparation of $C_8F_{17}OCF_2OC_3F_6H$ from $C_8F_{17}OCF_2OC_3F_6CO_2CH_3$ The precursor, $C_8H_{17}OCH_2OC_4H_8OH$ was prepared by monoalkylation of butane diol with octyl chloromethyl ether. The precursor was first acetylated with acetyl chloride in methylene chloride containing triethylamine and then fluorinated, and a portion of the crude perfluorinated product was hydrolyzed by treatment with aqueous sulfuric acid and then distilled to yield the carboxylic acid $C_8F_{17}OCF_2OC_3F_6CO_2H$, having a boiling range 100–106° C. at 1.1 torr. Differential scanning calorimetry revealed the acid had a $T_g$ of –97.0° C. and several crystalline exotherms of –77.4, –61.5 and –37.7° C. and a broad melting point at –9.0° C.

Another portion of the crude perfluorinated products was methanolysed essentially as in Example 1 to yield $C_8F_{17}OCF_2OC_3F_6CO_2CH_3$, having a boiling range 124–130° C. at 25 torr. The latter methyl ester was then decarboxylated using the procedure of Example 1 to yield $C_8F_{17}OCF_2OC_3F_6H$, having a boiling range of 178–183° C.; the structures of this hydride and the precursor fluorinated ester were confirmed by $^{19}F$ NMR.

EXAMPLE 30

Preparation of $C_8F_{17}O$—$(C_2F_4O)_2CF_2CO_2H$

The precursor was prepared by monoalkylation of triethylene glycol with octyl bromide, followed by acetylation. The precursor was fluorinated as in Example 1, hydrolyzed by treatment with aqueous sulfuric acid, and distilled, the product, $C_8F_{17}O$—$(C_2F_4O)_2CF_2CO_2H$, having a boiling range of 105–110° C. at 1.4 torr, and a melting point of 24° C.

EXAMPLE 31

Preparation of $HC_3F_6OC_3F_6H$ from $CH_3O(CO)C_3F_6OC_3F_6COOCH_3$

The starting diacetate, $CH_3C(O)OC_4H_8O$—$(C_4H_8O)_nC_4H_8OC(O)CH_3$, was prepared by acetylation of polytetramethylene glycol (average molecular weight of 250) with acetyl chloride. The diacetate was then converted to $CH_3OC(O)C_3F_6O$—$(C_4F_8O)_nC_3F_6COOCH_3$ by essentially the same fluorination and methanolysis procedures described in Example 1. 1400 g of the resulting mixture of diesters was distilled on a ten-plate glass-packed column to isolate $CH_3OC(O)C_3F_6OC_3F_6COOCH_3$.

278 g of the isolated fluorochemical was combined with 72 g of KOH in 250 mL of ethylene glycol. The resulting mixture was heated, distilled, and the product, $HC_3F_6OC_3F_6H$, was recovered essentially as in Example 1 (b.p. 84° C.). The structure of the product was confirmed by $^{19}F$ NMR.

EXAMPLE 32

Preparation of $n$-$C_{12}F_{25}OC_2F_4OC_2F_4OCF_2CO_2H$

The precursor, $n$-$C_{12}H_{25}O(C_2H_4O)_3H$, was prepared by monoalkylation of triethylene glycol with n-dodecyl bromide. After acetylation, the resulting product was fluorinated essentially as in Example 1, and the fluorinated product was concentrated and treated with 55.0 g NaOH in 300 mL water. After heating for 5 hours on a steam bath, the product was acidified with an excess of a 50 weight percent solution of $H_2SO_4$ in water and then extracted with Fluorinert™ FC-75 perfluorinated liquid (a mixture of $C_8$ perfluorochemicals, b.p. 103° C.) which had been heated to about 60° C. on a steam bath. Distillation yielded pure $n$-$C_{12}F_{25}OC_2F_4OC_2F_4OCF_2CO_2H$ ($T_g$=–62.7° C. and $T_m$=69.2° C. by DSC).

EXAMPLE 33

Preparation of

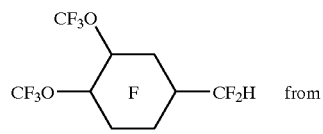

from

-continued

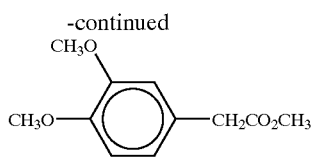

The starting material, methyl 2-(3,4-dimethoxyphenyl) acetate was fluorinated essentially as in Example 1 to yield perfluoro-2-(3,4-dimethoxycyclohexyl) acetic acid after hydrolysis. This was then decarboxylated essentially as described in Example 1 to the perfluorinated ether hydride.

EXAMPLE 34

Preparation of

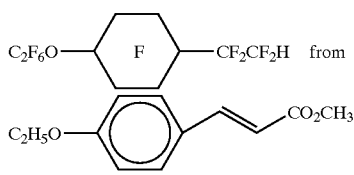

The starting material, methyl 3-(4-ethoxyphenyl)-trans-2-propenoate was prepared by condensation of 4-ethoxybenzaldehyde with malonic acid, followed by esterification. This methyl ester was fluorinated, methanolyzed, and decarboxylated essentially as in Example 1 to produce the perfluorinated ether hydride.

EXAMPLE 35

Preparation of

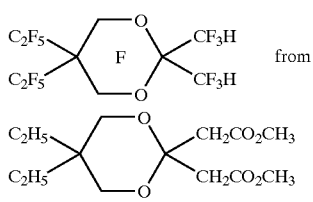

The starting material was prepared by condensation of 2,2-diethyl propane diol with dimethyl 3-oxoglutarate. This dimethyl ester was fluorinated, methanolyzed to the diester, and decarboxylated essentially as in Example 1 to produce the perfluorinated ether dihydride.

EXAMPLE 36

Preparation of

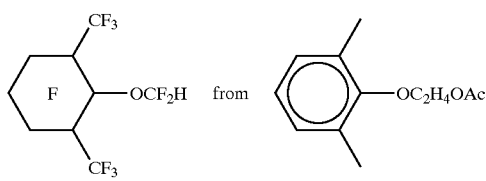

The starting material was prepared by reaction of 2,6-dimethylphenol with ethylene carbonate and subsequent acetylation with acetyl chloride. This acetate was fluorinated, methanolyzed, and decarboxylated essentially as in Example 1 to produce the perfluorinated ether hydride (b.p. 132° C.).

EXAMPLE 37

Preparation of

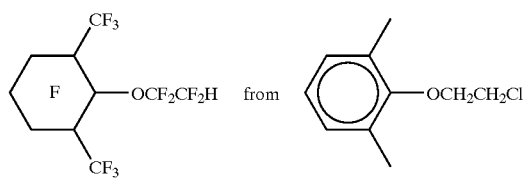

The starting material was prepared by the treatment of 2-(2,6-dimethylphenyloxy)ethanol (from Example 36) with thionyl chloride. This was fluorinated essentially as in Example 1, followed by Raney Ni reduction of the chloride essentially as described in Example 12 to produce the perfluorinated ether hydride.

EXAMPLE 38

Preparation of

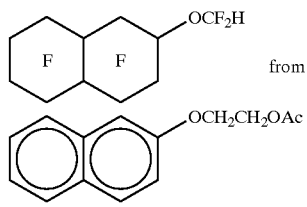
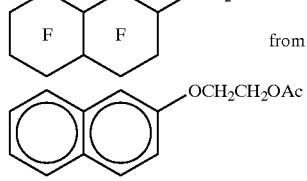

The starting material was prepared from the addition of β-napthol to ethylene carbonate, followed by acetylation with acetyl chloride. This acetate was fluorinated, methanolyzed, and decarboxylated essentially as in Example 1 to produce the perfluorinated ether hydride (b.p. 171° C.).

EXAMPLE 39

Preparation of $C_5F_{11}OCF_2C(CF_3)_2CF_2H$ from $C_5H_{11}OCH_2C(CH_3)_2CH_2Cl$ The starting material was prepared essentially as described above in Example 11. The ether chloride was fluorinated essentially as in Example 1, followed by Raney Ni reduction of the chloride essentially as described in Example 11 to produce the perfluorinated ether hydride (b.p. 148° C.).

EXAMPLE 40

Preparation of $(C_4F_9O)_2CFCF_2H$ from $(C_4H_9O)_2CHCH_2Cl$

The starting material was prepared by the addition of n-butanol to 2-chloroacetaldehyde and was fluorinated essentially as in Example 1, followed by Raney Ni reduction of the chloride essentially as described in Example 11 to produce the perfluorinated ether hydride.

EXAMPLE 41

Preparation of $CF_3O(CF_2)_9H$ from $CH_3O(CH_2)_{10}OAc$

The starting material was prepared by monoalkylation of 1,10-decanediol with dimethyl sulfate, followed by acetylation with acetyl chloride. This acetate was fluorinated, hydrolyzed, and decarboxylated essentially as in Example 1 to produce the perfluorinated ether hydride.

EXAMPLE 42

Preparation of $C_9F_{19}OCF_2H$ from $C_9H_{19}OC_2H_4OAc$

The starting material was prepared by monoalkylation of ethylene glycol with n-nonyl bromide, followed by acetylation with acetyl chloride. This acetate was fluorinated, hydrolyzed, and decarboxylated essentially as in Example 1 to produce the perfluorinated ether hydride (b.p. 155° C.).

EXAMPLE 43

Preparation of $(iso-C_3F_7)_2CFOC_2F_4H$ from $(iso-C_3H_7)_2CHOC_2H_4CO_2CH_3$ The starting material was prepared by Michael addition of 2,4-dimethyl-3-pentanol to acrylonitrile, followed by methanolysis to the methyl ester. This ester was fluorinated, hydrolyzed, and decarboxylated essentially as in Example 1 to produce the perfluorinated ether hydride.

EXAMPLE 44

Preparation of

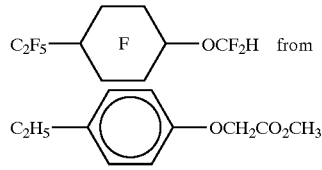 from

The starting material was prepared by the alkylation of 4-ethylphenol with methyl chloroacetate. This ester was fluorinated, hydrolyzed, and decarboxylated essentially as in Example 1 to produce the perfluorinated ether hydride (b.p. 131° C.).

EXAMPLE 45

Comparative Atmospheric Lifetimes and Boiling Points

The atmospheric lifetime of various sample compounds was calculated by the technique described in Y. Tang, *Atmospheric Fate of Various Fluorocarbons*, M. S. Thesis, Massachusetts Institute of Technology (1993). As shown in the table below, the atmospheric lifetime of an ether hydride compound having two or more carbon atoms between the ether oxygen atom and the terminal hydrogen atom is considerably shorter than the atmospheric lifetimes of ether hydride compounds having only one carbon atom between the ether oxygen atom and the terminal hydrogen atom. Because of the shorter atmospheric lifetimes of the compounds of the present invention, these compounds are more environmentally acceptable.

| Compound | Atmospheric Lifetime (yrs) |
|---|---|
| $C_6F_{13}OC_2F_4OCF_2H$ | >170 |
| $C_4F_9OC_2F_4OCF_2H$ | >170 |
| $C_8F_{17}OCF_2CF_2H$ | 80 |

In addition, as shown in the table below, ether hydride compounds having two or more carbon atoms between the ether oxygen atom and the terminal hydrogen atom have lower boiling points than analogous non-ether compounds, and significantly lower boiling points than analogous ether hydride compounds having only one carbon atom between the ether oxygen atom and the terminal hydrogen atom. The unexpectedly low boiling points of compounds of the present invention render the compounds useful in processes involving temperature-sensitive substrates such as plastics. (For example, in vapor-phase cleaning, a substrate is rinsed in the condensing vapor of a boiling fluid, and in condensation heating, a substrate is heated by immersion in a boiling fluid.) In such applications, a lower-boiling fluid is preferred so as to avoid damage to the substrate. While it is known that boiling points can be reduced by selection of a compound having fewer carbon atoms, this may result in a boiling point reduction of 25° C. or more, in addition to adversely affecting other properties such as solvency.

| Compound | Boiling Point (° C.) |
|---|---|
| $C_8F_{17}CF_2H$ | 136 |
| $C_8F_{17}OCF_2H$ | 139 |
| $C_7F_{15}OC_2F_4H$ | 131 |
| F—C$_3$F$_6$H (phenyl) | 126 |
| F—C$_2$F$_4$OCF$_2$H (phenyl) | 134 |
| C$_2$F$_5$—F—OCF$_2$H (phenyl) | 131 |
| F—CF$_2$OC$_2$F$_4$H (phenyl) | 125 |
| $C_9F_{19}CF_2H$ | 154 |
| $C_9F_{19}OCF_2H$ | 155 |
| $C_8F_{17}OC_2F_4H$ | 148 |
| $C_6F_{13}OC_4F_8H$ | 149 |
| $C_5F_{11}OC_5F_{10}H$ | 150 |

Various modifications and alterations of this invention will become apparent to those skilled in the art without departing from the scope and spirit of this invention.

What is claimed is:

1. In a method of vapor phase soldering wherein a component to be soldered is immersed in or enveloped by a body of fluorinated liquid vapor to melt the solder, and the component is then withdrawn from the body of vapor, the improvement comprising using as the fluorinated liquid a composition comprising at least one normally liquid omega-hydrofluoroalkyl ether compound having a saturated perfluoroaliphatic chain of carbon atoms interrupted by one or more ether oxygen atoms, the chain carbon atom at one end (the proximal end) of the chain being that of a difluoromethyl group which is bonded to another chain carbon atom or to a said ether-oxygen atom, the carbon atom at the other end (the distal end) of the chain being part of a distal group selected from the group consisting of difluoromethyl, difluorochloromethyl, a straight-chain perfluoroalkyl, a branched-chain perfluoroalkyl, and a perfluoroalkyl substituted with a saturated perfluoroalicyclic moiety, with the proviso that where said difluoromethyl group at the proximal end is bonded to a said ether-oxygen atom, then said straight-chain perfluoroalkyl has at least 6 chain carbon atoms and said branched-chain perfluoroalkyl has at least 4 carbon atoms.

2. The process of claim 1 wherein said normally liquid omega-hydrofluoroalkyl ether compound is represented by the general formula:

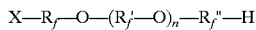

wherein:

H is a primary hydrogen atom;

X is a fluorine atom, a primary hydrogen atom, or a primary chlorine atom;

n is an integer of 0 to 7; and $R_f$, $R_f'$, and $R_f''$ are independently selected from the group consisting of linear or branched, unsubstituted perfluoroalkylene groups; linear or branched, perfluoroalkyl- or perfluorocycloalkyl-substituted perfluoroalkylene groups; and linear or branched perfluoroalkylene groups substituted with an ether oxygen-containing moiety;

with the proviso that when X is H or Cl, $R_f$ has 1 to 18 chain carbon atoms, $R_f'$ has 1 to 12 chain carbon atoms, and $R_f''$ has 2 to 12 chain carbon atoms;

and with the further proviso that when X is F, then $R_f$ has at least 4 chain carbon atoms, $R_f'$ has 1 or more chain carbon atoms, and $R_f''$ has 2 or more chain carbon atoms.

3. The process of claim 2 wherein said X is a fluorine atom.

4. The process of claim 2 wherein said normally liquid omega-hydrofluoroalkyl ether compound is represented by the formula:

X—$R_f$—O—($CF_2CF_2$—O)$_m$—$R_f''$—H where m is an integer of 0 to 7, and H, X, $R_f$, and $R_f''$ are as defined in claim 2.

5. The process of claim 2 wherein said normally liquid omega-hydrofluoroalkyl ether compound is represented by the formula:

F—$R_f$—O—($R_f'$—O)$_p$—$R_f''$—H where p is an integer of 0 to 2, and H, $R_f$, $R_f'$, and $R_f''$ are as defined in claim 2, except that $R_f$ has 4 to 12 chain carbon atoms, $R_f'$ has 1 to 12 chain carbon atoms, and $R_f''$ has 2 to 12 chain carbon atoms.

6. The process of claim 2 wherein said normally liquid omega-hydrofluoroalkyl ether compound is represented by a formula selected from the group consisting of
$C_8F_{17}$—O—$C_2F_4H$, $C_7F_{15}$—O—$C_2F_4H$, $C_6F_{13}$—O—$C_2F_4$—O—$CF_2H$, $C_4F_9$—O—$C_2F_4H$, $HCF_2CF_2$—O—$CF_2CF_2$—O—$CF_2CF_2H$, $C_4F_9$—O—$(CF_2)_5H$, $C_5F_{11}$—O—$(CF_2)_5H$, $C_8F_{17}$—O—$(CF_2)_5H$, $C_4F_9$—O—$CF_2C(CF_3)_2CF_2H$, $H(CF_2)_4$—O—$(CF_2)_4H$, $Cl(CF_2)_4$—O—$(CF_2)_4H$, $C_6F_{13}$—O—$C_2F_4H$, $C_4F_9$—O—$(CF_2)_4$—O—$(CF_2)_3H$, $(C_2F_5)_2CFCF_2$—O—$C_2F_4H$, c-$C_6F_{11}CF_2$—O—$C_2F_4H$, $C_4F_9$—O—$C_2F_4$—O—$C_3F_6H$, $C_6F_{13}$—O—$C_4F_8H$, $C_6F_{13}$—O—$C_3F_6H$, $C_5F_{11}$—O—$(CF_2)_4H$, $C_4F_9$—O—$C_3F_6H$, $C_8F_{17}OCF_2OC_3F_6H$, $HC_3F_6OC_3F_6H$,

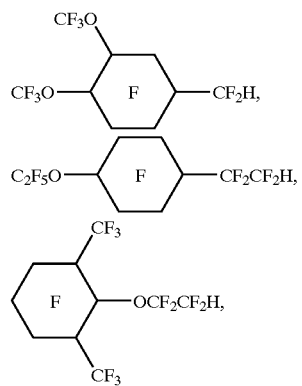

$C_5F_{11}OCF_2C(CF_3)_2CF_2H$, $(C_4F_9O)_2CFCF_2H$, $CF_3O(CF_2)_9H$, and $(iso-C_3F_7)_2CFOC_2F_4H$.

7. The process of claim 1 wherein said normally liquid omega-hydrofluoroalkyl ether compound is represented by the general formula:

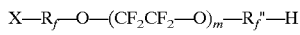

wherein:

H is a primary hydrogen atom;

X is a fluorine atom, a primary hydrogen atom, or a primary chlorine atom;

n is an integer of 0 to 7; and $R_f$, $R_f'$, and $R_f''$ are independently selected from the group consisting of linear or branched, unsubstituted perfluoroalkylene groups; linear or branched, perfluoroalkyl- or perfluorocycloalkyl-substituted perfluoroalkylene groups; and linear or branched perfluoroalkylene groups substituted with an ether oxygen-containing moiety;

with the proviso that when X is H or Cl, $R_f$ has 1 to 18 chain carbon atoms and each of $R_f'$ and $R_f''$ independently has 1 to 12 chain carbon atoms; and with the further proviso that when X is F, then $R_f$ has at least 4 chain carbon atoms, and each of $R_f'$ and $R_f''$ independently has 1 or more chain carbon atoms;

and with the still further proviso that when n is zero, then $R_f$ is a perfluorocycloalkyl-substituted perfluoroalkylene group.

* * * * *

UNITED STATES PATENT AND TRADEMARK OFFICE
CERTIFICATE OF CORRECTION

PATENT NO. : 6,863,211 B2
DATED : March 8, 2005
INVENTOR(S) : Moore, George G. I.

It is certified that error appears in the above-identified patent and that said Letters Patent is hereby corrected as shown below:

Column 8,
Line 12, delete "nitrites" and insert -- nitriles --.

Column 10,
Line 35, delete "and" before "water- free".

Column 25,
Line 20, delete "$C_2F_6O$" and insert -- $C_2F_5O$ --.

Line 39, delete " 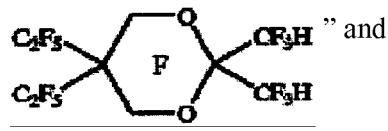 " and insert -- 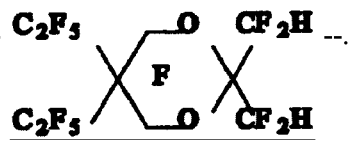 --.

Signed and Sealed this

Sixth Day of June, 2006

JON W. DUDAS
*Director of the United States Patent and Trademark Office*